United States Patent [19]

Payne et al.

[11] Patent Number: 5,521,286
[45] Date of Patent: *May 28, 1996

[54] BACILLUS THURINGIENSIS ISOLATE DENOTED B.T. PS81F, ACTIVE AGAINST LEPIDOPTERAN PESTS, AND A GENE ENCODING A LEPIDOPTERAN-ACTIVE TOXIN

[75] Inventors: Jewel Payne; August J. Sick, both of San Diego, Calif.

[73] Assignee: Mycogen Corporation, San Diego, Calif.

[ * ] Notice: The term of this patent shall not extend beyond the expiration date of Pat. No. 5,039,523.

[21] Appl. No.: 277,721

[22] Filed: Jul. 20, 1994

Related U.S. Application Data

[62] Division of Ser. No. 153,840, Nov. 17, 1993, Pat. No. 5,336,492, which is a continuation of Ser. No. 629,504, Dec. 18, 1990, abandoned, which is a division of Ser. No. 263,567, Oct. 27, 1988, Pat. No. 5,045,469.

[51] Int. Cl.$^6$ .................. C07K 14/325; A01N 63/02; C12N 15/33
[52] U.S. Cl. .................. 530/350; 536/23.71; 514/12; 435/71.3; 424/93.461
[58] Field of Search .................. 530/350; 536/23.71; 514/12; 435/71.3; 424/93.461

[56] References Cited

U.S. PATENT DOCUMENTS

| | | | |
|---|---|---|---|
| 4,448,885 | 5/1984 | Schnepf et al. | 435/252.33 |
| 4,467,036 | 8/1984 | Schnepf et al. | 435/320.1 |
| 5,039,523 | 8/1991 | Payne et al. | 424/93.461 |
| 5,273,746 | 12/1993 | Payne et al. | 424/93.461 |

FOREIGN PATENT DOCUMENTS 0370994  3/1989  European Pat. Off. .

OTHER PUBLICATIONS

Schnepf, H. E., H. R. Whiteley (1981) "Cloning and expression of the *Bacillus thuringiensis* crystal protein gene in *Escherichia coli*" Proc. Natl. Acad. Sci. USA 78(5):2893–2897.

Liao, C. X., et al., "Antirejection Therapy with *Tripterygium wolfordii* and Low–Dose Cyclosporin A in Small Bowel Transplantation in Pigs," *Bull. Jinling Hosp.* 6:365 (1992).

Hueston, J. T., *Dupuytren's Disease*, Ch. 25. Enzymic Fasciotomy, 1974, pp. 141–143. Grune & Stratton, Inc., New York, NY.

Ramamurthy, et al., "Chemically–Modified Tetracycline Normalizes Collagen Metabolism in Diabetic Rats: a Dose–Response Study", *J. Peridont Res.*, 28: 420–428 (1993).

Schneir, et al., "Minocycline–Treatment of Diabetic Rats Normalizes Skin Collagen Production and Mass: Possible Causative Mechanisms", *Matrix*, 10: 112–123 (1990).

Engesaeter, et al., "Effects of Oxytetracycline on Solubility and Synthesis of Collagen in Young Rats", *Acta Orthop. Scand.*, 51: 43–48 (1980).

*Primary Examiner*—Robert A. Wax
*Assistant Examiner*—Rebecca Prouty
*Attorney, Agent, or Firm*—Saliwanchik & Saliwanchik

[57] ABSTRACT

A novel *B.t.* toxin gene toxic to lepidopteran insects has been cloned from a novel lepidopteran-active *B. thuringiensis* microbe. The DNA encoding the *B.t.* toxin can be used to transform various prokaryotic and eukaryotic microbes to express the *B.t.* toxin. These recombinant microbes can be used to control lepidopteran insects in various environments.

3 Claims, 8 Drawing Sheets a b c d a. *B.t.* PS81F uncut
b. *B.t.* PS81F cut with HindIII
c. *B.t.* HD-1 uncut
d. *B.t.* HD-1 cut with HindIII

Fig. 2A

```
HD1   - WHITELEY'S "4.5" GENE
HD73  - ADANG'S "6.6" GENE
BTB   - BULLA'S "5.3" GENE

81F   - MYCOGEN'S 81F TOX GENE
BTE   - HONEE'S ENTOMOCIDUS TOX GENE
HD2   - BRIZZARD'S HD2 TOX GENE
```

```
      1       5         10        15        20        25        30        35        40        45        50        55
HD1   M D N N P N I N E C I P Y N C L S N P E V E V L G G E R I E T G Y T P I D I S L S L T Q F L L S E F V P G A G
HD73  - - - - - - - - - - - - - - - - - - - - - - - - - - - - - - - - - - - - - - - - - - - - - - - - - - - - - - -
BTB   - - - - - - - - - - - - - - - - - - - - - - - - - - - - - - - - - - - - - - - - - - - - - - - - - - - - - - -
81F   - E I V N - Q - Q - V - - - - - - N - - - N - I - D I - - S N S T = V A T N - A - E I S R = - - A S A T - I G -
BTE   - E E N N Q = - Q - - - - - - - - - - - - E V L - D - - - - S - - N S S - - - - - - - V - - - V - N - - - - G -
HD2   - T S N R*- E - - I - N A V S N H S A Q M D L - P D A - - - D S*S T V Q T G I N I A G R I - G V L V - - F - -
              * K                                                      * L C I S E G N N I D P F V S A 56      60        65        70        75        80        85        90        95        100       105       110
HD1   F V L G L V D I I W G I F G P S Q W D A F P V Q I E Q L I N Q R I E E F A R N Q A I S R L E G L S N L Y Q I Y
HD73  - - - - - - - - - - - - - - - - - - - - - L - - - - - - - - - - - - - - - - - - - - - - - - - - - - - - - - -
BTB   - - - - - - - - - - - - - - - - - - - - - L - - - - - - - - - - - - - - - - - - - - - - - - - - - - - - - - -
81F   I L - - - F - A - - - S I - - - - - - - L - L E - - - L - - D - K - - - - - - - - - - - - - - - I - S - - G - -
BTE   - L V - - I - F V - - - V - - - - - - - - - L - - - - - - - - E - - G - - - - - A - - A N - - - - G - N F N - -
HD2  *Y S F = - - G E L - P R = - R D - - E I - L E H V - - - - - - Q - T - N - - - T - L A - - Q - - G D S F R A -
     * Q L A S F 111     115       120       125       130       135       140       145       150       155       160       165
HD1   A E S F R E W E A D P T N P A L R E E M R I Q F N D M N S A L T T A I P L L A V Q N Y Q V P L L S V Y V Q A A
HD73  - - - - - - - - - - - - - - - - - - - - - - - - - - - - - - - - - - - - - F - - - - - - - - - - - - - - - - -
BTB   - - - - - - - - - - - - - - - - - - - - - - - - - - - - - - - - - - - - - F - - - - - - - - - - - - - - - - -
81F   T - A - - - - - - - - - - - - - K - - - - T - - - - - - - I - V - - - - - F S - - - - - - - F - - - - - - - -
BTE   V - A - K - - - E - - N - - E T - T R V I D R - R I L D G L - E R D - - S F R I S G F E - - - - - - - A - - -
HD2   Q Q - L E D - L E N R D D A R T - S V L Y T - Y I A L E L D F L N - M - - F - I R - Q E - - - - M - - A - - -
```

```
       606                     615                    625                       635                      645                   655          660
HD1    N F S S V F T L S A H V F N S G N E V Y I D R I E F V P A E V T F E A E Y D L E R A Q K A V N E L F T S
HD73   - G S N I - = I R G I I - - R N - I G T A G - I - I - L I - I F - L - I I I I - I I I I I I I I I I I I
BTB    T - L - - I I I - I - I - I I - - - I I - I - K - L - L I I - - A - - I I - I I - - A - I I I
81F    S - A N P D D I I I P D D I - P L - G A G * - L - - L I L - D A I - I - I I - I I - A - I I I
BTE    S - A N P R I I I - - I - I - F G * I S I S S G - - I I I I D A - E I I I S I I I I - A - I I I
HD2    T F T Q I Q D I I R T - I Q G L S G G N G - - K - - I - V T A - A - - - - - - - - N - - - - A - - - -
```

```
       661                     670                    680                       690                      700                   710          715
HD1    S N Q I G L K T D V T D Y H I D Q V S N L V E C L S D E F C L D E K Q E L S E K V K H A K R L S D E R N L L Q
HD73   T - L - - - - - - - - I - - - - - - - - - I T Y - - - - - - - I R I I - I I I I I I I I I I I I I
BTB    T - I - - - - - - - - I - - - - - - - - - I - - - - - - - - - - R I I I I I I I I I I I I I I I
81F    T - I - - - - - - - - I - - - - - - - - - I D - - - - - - - - - R I I I I I I I I I I I I I I I
BTE    T - - - - - - - - - - I - - - - - - - - - I A - - - - - - - - - - I I I I I - L I I I I I I I I
HD2    - P R R - - - - - - - - - - - - - - - - - - - - - - - - - - - - - - - - - - - - Y - - - - - - - E - - -
```

```
       716                     725                    735                       745                      755                   765          770
HD1    D P N F R G I N R Q L D R G W R G S T D I T I Q G G D D V F K E N Y V T L L G T F D E C Y P T Y L Y Q K I D E
HD73   - - - - - - - - - - - - - - - - - - - - - - - - - - - - - - - - - - S - P - - - - - - - - - - - - -
BTB    - - - - - - - - - - - - - - - - - - - - - - - - - - - - - - - - - - - - P - - - - - - - - - - - - -
81F    - - - K - - - - - - - P - - - - - - - - - - - - - - - - - - - - - - - - - - - - - - - V - - - - - - -
BTE    - - - - - - - - - - - P - - - - - - - - - - - - - - - - - - - - - - - - - - - - - - - - A - - - - - G
HD2    T S - - - K - - P D * H * F I S T N E Q S N F T S I H E Q S E N - - - - - - - - - - - - - - - - - - - -
```

```
       771                     780                    790                       800                      810                   820          825
HD1    S K L K A Y T R Y Q L R G Y I E D S Q D L E I Y L I R Y N A K H E T V N V P G T G S L W P L S A Q S P I G K C
HD73   - F - - - - - - - - - - - - - - - - - - - - - - - - - - - - - - - - - - - - - - - - - - - - - - -
BTB    - - - - - - - - - - - - - - - - - - - - - - - - - - - - - - - - - - - - - - - - - - - - - - - - -
81F    - - - - - - - - - - - - - - - - - - - - - - - - - - - - - - - - - - - - - - - - - - - - - - - - -
BTE    - - - E - - - - E - - - - - - - - - - - - - - - - - - - - - - - - - - - - - - - - - - - - - - - -
HD2    - - - - - - - - - - - - - - - - - - - - - - - - - - - - - - - - - I - L D - - - - - - - - - V E - - R
```

Fig. 2E

```
           826                                                          880
      HD1   G E P N R C A P H L E W N P D L D C S C R D G E K C A H H S H H F S L D I D V G C T D L N E D L G V W V I F K
      HD73  - - - - - - - - - - - - - - - - - - - - - - - - - - - - - - - - - - - - - - - - - - - - - - - - - - - - - -
      BTB   - = - - - - - - - - = - = = = = = = = = - - - = - - = - - - - - - - - - - - - - - - - - - - - - - - - - - -
      81F   - - - - - - - - - - - - - - - - - - - - - - - - - - - - - - - - - - - - - - - - - - - - - - - - - - - - - -
      BTE   - - - - - - - - - - - - N - - - - - - - - - - - - - - - - - - - - - - - H - - - - - - - - - - - - - - - - -
      HD2   - - - - - - - - F - - - - V - - - - - - - - - - - - - - - - - - T - - - - - - - - - - - - - - - - - - - - V 881                                                          935
      HD1   I K T Q D G H A R L G N L E F L E E K P L V G E A L A R V K R A E K K W R D K R E K L E W E T N I V Y K E A K
      HD73  - - - - - - - - - - - - - - - - - - - - - - - - - - - - - - - - - - - - - - - - - - - - - - - - - - - - - -
      BTB   - - - - - - - Y - - - - - - - - - - - - - - - - - - - - - - - - - - - - - C - - - - - Q L - - - - - - - - - -
      81F   - - - - - E - - - - - - - - - I - - - - - - - - - - S - - - - - - - - - - - - - - - - Q L - - - - - K R - - -
      BTE   - - - - - - - - - - - - - - - - - - - - - - - - - - - - - - - - - - - - - - - - - - - - - - - - - - - - T - -
      HD2   - - - - - - - - - - - - - - - - - - - - - - - - L L L - - - - - - - - - - - - - - - - - - - - - - - - - - - -

936                                                          990
      HD1   E S V D A L F V N S Q Y D Q L Q A D T N I A M I H A A D K R V H S I R E A Y L P E L S V I P G V N A A I F E E
      HD73  - - - - - - - - - - - - - R - - - - - - - - - - - - - - - - - - - - - - - - - - - - - - - - - - - - - - - -
      BTB   - - - - - - - - - - - - - R - - - - - - - - - - - - - - - - - - - - - - - - - - - - - - - - - - - - - - F -
      81F   - - - - - - - - - - - - - R - - V - - - - - - - - - - - - - R - - - - - - - - S - - - - - - - - - - - - - - -
      BTE   - A - - - - - - - - - - D - - - - - - - - - - - - G - - - - R - - - - - - - - - - - P - - - - - - - - - - - E
      HD2   - - - - - - - - - - - - - R - - - - - - - - - - - - - - - L - - - - - - - - - - - - - - - - - - - - - - - - -

991                                                          1045
      HD1   L E G R I F T A F S L Y D A R N V I K N G D F N N G L S C W N V K G H V D V E E Q N N Q R S V L V L P E W E A
      HD73  - - - - - - - - - - - - - - - - - - - - - - - - - - - - - - - - - - - - - - - - - - - - - - - - - - - - - -
      BTB   - - - - - - - - - - - - - - - - - - - - - - - - - - - - - - - - - - - - - - - - - - - - - - - - - - - - - -
      81F   H - - - - - - - - - - Y - - - - - - - - - - - - - - - - - - - - - - - - - - - - - H - - - - - - V V I - - - -
      BTE   - - - - - - - - - - - - - - - - - V - - - - - - - - - - - - - - - - - L - - - - - = Q - - - H - - V - - - - -
      HD2   - - - - - - - - - - - - - - - - - - - - - - - - - - - - - - - - - - - T - - - - - - - - S H H - - I - D - - -
```

Fig. 2F

```
       1046          1050          1055          1060          1065          1070          1075          1080          1085          1090          1095          1100
HD1     E  N  V  S  Q  E  V  R  V  C  P  G  R  G  Y  I  L  R  V  T  A  Y  K  E  G  Y  G  E  G  C  V  T  I  H  E  I  E  N  N  T  D  E  L  K  F  S  N  C  V  E  E  I  Y  P  N
HD73    -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -
BTB     -  -  -  -  -  -  -  -  -  -  -  -  -  -  -  -  -  -  -  -  -  -  -  -  -  -  -  -  -  -  -  -  -  -  -  -  -  -  -  D  -  -  -  -  -  -  -  -  -  -  -  -  -  -
81F     -  -  -  -  -  -  -  -  -  -  -  -  -  -  -  -  -  -  -  -  -  -  -  -  -  -  -  -  -  -  -  -  -  -  -  -  -  -  -  D  -  -  -  -  -  -  -  -  -  -  V  -  -  -
BTE     -  -  -  A  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  V  -  -  -
HD2     -  -  -  -  -  -  -  -  -  -  -  -  C  -  -  -  -  -  -  -  -  -  -  -  -  -  -  -  -  -  -  -  -  -  -  -  -  -  -  -  -  -  -  -  -  K  -  R  E  -  V  -  -  T 1101          1105          1110          1115          1120          1125          1130          1135          1140          1145          1150          1155
HD1     N  T  V  T  C  N  D  Y  T  V  N  Q  E  E  Y  G  G  A  Y  T  S  R  N  R  G  Y  N  E  A  P  S  V  P  A  D  Y  A  S  V  Y  E  E  K  S  Y  T  D  G  R  R  E
HD73    -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -
BTB     -  -  -  -  -  -  -  -  -  A  -  -  -  -  -  H  -  -  -  -  -  -  -  -  -  -  -  D  G  -  -  =  =  -  -  -  -  -  -  -  -  -  -  A  -  -  -  -  -  -  -
81F     -  -  -  -  -  -  -  -  -  A  -  -  -  -  -  H  -  -  T  -  -  -  -  -  -  -  -  D  D  -  =  =  N  -  -  -  -  -  -  -  -  -  -  A  -  -  -  -  R  -  -
BTE     -  N  -  -  -  -  -  -  -  -  -  -  -  I  -  G  T  A  -  -  -  -  -  Q  -  -  -  -  -  -  N  =  =  N  -  -  -  -  -  -  -  -  -  -  -  -  -  -  -  -  -
HD2     -  -  -  -  -  -  -  -  -  -  -  -  -  -  -  A  H  -  -  -  -  -  -  A  -  -  -  E  D  -  Y  =  =  T  T  A  S  V  N  -  K  P  T  -  -  -  E  T  -  V  -  -

1156          1160          1165          1170          1175          1180          1185          1190          1195
HD1     N  P  C  E  F  N  R  G  Y  R  D  Y  T  P  L  P  V  G  Y  V  V  T  K  E  L  E  Y  F  P  E  T  D  K  V  W  I  E  I  G  E  T  E  G  T  F  I  V  D  S  V  E  L  L  M  E
HD73    -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -
BTB     -  -  -  -  -  S  -  G  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -
81F     -  -  -  -  -  S  -  G  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -  -
BTE     -  -  -  -  -  -  -  -  -  -  -  -  -  -  I  -  -  -  -  -  -  -  -  -  -  D  -  -  -  -  -  -  -  -  -  -  -  -  -  -  -  -  -  -  -  -  -  -  -  -  -  -  -  -  -
HD2     -  H  -  -  -  -  -  -  -  -  -  -  -  -  -  Y  P  -  V  -  A  -  -  -  -  -  -  -  -  -  -  -  -  T  -  -  -  -  -  -  -  -  -  -  -  -  -  -  -  -  -  -  -  -  K
```

Fig. 2G

HD1 is the cryA1 toxin gene from Bacillus thuringiensis subsp. kurstaki HD1 (Brizzard and Whiteley, Nucleic acids Research 16(1988)2723).

HD73 is the cryA3 gene from HD73.

BTB is the cryA2 gene from BT strain Berliner.

81F is a delta endotoxin gene from Mycogen's BT strain PS81F.

BTE is a delta endotoxin gene from BT subspecies entomocidus (Honee, Salm and Visser, Nucleic Acids Research 16(1988)6240).

HD2 is a delta endotoxin gene from BT strain HD2 (Brizzard and Whiteley, Nucleic Acids Research 16(1988)2723).

- - - - denote identical amino acid homologies.

= = = = denote gaps required to align sequences with HD1.

* denote inserts required to align the sequences BTE and HD2 with HD1.

5,521,286

BACILLUS THURINGIENSIS ISOLATE DENOTED B.T. PS81F, ACTIVE AGAINST LEPIDOPTERAN PESTS, AND A GENE ENCODING A LEPIDOPTERAN-ACTIVE TOXIN

CROSS-REFERENCE TO RELATED APPLICATIONS

This is a division of application Ser. No. 08/153,840, filed Nov. 17, 1993, now U.S. Pat. No. 5,336,492, which was a continuation of application Ser. No. 07/629,504, filed Dec. 18, 1990, now abandoned, which was a division of application Ser. No. 07/263,567, filed Oct. 27, 1993, now U.S. Pat. No. 5,045,469, issued Sep. 3, 1991.

BACKGROUND OF THE INVENTION

The most widely used microbial pesticides are derived from the bacterium *Bacillus thuringiensis*. This bacterial agent is used to control a wide range of leaf-eating caterpillars, and mosquitos. *Bacillus thuringiensis* produces a proteinaceous paraspore or crystal which is toxic upon ingestion by a susceptible insect host. For example, *B. thuringiensis* var. kurstaki HD-1 produces a crystal called a delta toxin which is toxic to the larvae of a number of lepidopteran insects. The cloning and expression of this *B.t.* crystal protein gene in *Escherichia coli* has been described in the published literature (Schnepf, H. E. and Whitely, H. R. [1981] Proc. Natl. Acad. Sci. USA 78:2893–2897). U.S. Pat. No. 4,448,885 and U.S. Pat. No. 4,467,036 both disclose the expression of *B.t.* crystal protein in *E. coli*.

BRIEF SUMMARY OF THE INVENTION

The subject invention concerns a novel *Bacillus thuringiensis* isolate designated *B.t.* PS81F which has activity against all lepidopteran pests tested.

Also disclosed and claimed is a novel toxin gene toxic to lepidopteran insects. This toxin gene can be transferred to suitable hosts via a plasmid vector.

Specifically, the invention comprises a novel *B.t.* isolate denoted *B.t.* PS81F, mutants thereof, and a novel delta endotoxin gene which encodes a 133,266 dalton protein which is active against lepidopteran pests.

BRIEF DESCRIPTION OF THE DRAWINGS

FIGS. 2A–2G. A comparison of the deduced amino acid sequence of 81F and five other known *B.t.* endotoxins.

BRIEF DESCRIPTION OF THE SEQUENCES

Figure 1:
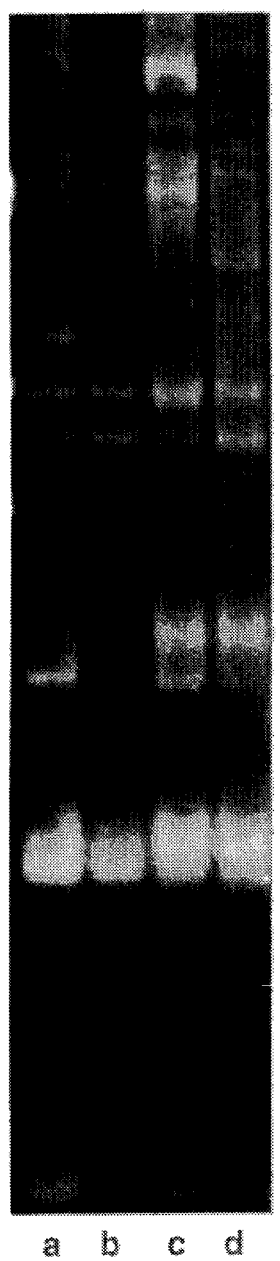
FIG. 1. Agarose gel electrophoresis of plasmid preparations from *B.t.* PS81F and *B.t.* HD-1.

SEQ ID NO. 1 is the combined nucleotide sequence and deduced amino acid sequence of the novel toxin.

SEQ ID NO. 2 is the nucleotide sequence of the novel toxin encoding gene.

SEQ ID NO. 3 is the deduced amino acid sequence of the novel toxin.

SEQ ID NO. 4 is a synthetic oligonucleotide used according to the subject invention.

DETAILED DISCLOSURE OF THE INVENTION

The novel toxin gene of the subject invention was obtained from a novel lepidopteran-active *B. thuringiensis* (*B.t.*) isolate designated PS81F.

Characteristics of *B.t.* PS81F

Colony morphology—Large colony, dull surface, typical *B.t.*

Vegetative cell morphology—typical *B.t.*

Flagellar serotype—4a4c, kenya.

Intracellular inclusions—sporulating cells produce a bipyramidal crystal.

Plasmid preparations—agarose gel electrophoresis of plasmid preparations distinguishes *B.t.* PS81F from *B.t.* HD-1 and other *B.t.* isolates.

Alkali-soluble proteins—*B.t.* PS81F has a 130,000 dalton protein and a 60,000 dalton protein.

Activity—*B.t.* PS81F kills all Lepidoptera tested.

| Bioassay results: | LC50 |
|---|---|
| Beet armyworm, *Spodoptera exigua* | 10.4 ug/ml |
| Western spruce budworm, *Choristoneura occidentalis* | 1.4 ug/ml |

Bioassay procedures:

*Spodoptera exigua*—dilutions are prepared of a spore and crystal pellet, mixed with USDA Insect Diet (Technical Bulletin 1528, U.S. Department of Agriculture) and poured into small plastic trays. Neonate *Spodoptera exigua* larvae are placed on the diet mixture and held at 25° C. Mortality is recorded after six days.

*Choristoneura occidentalis*—dilutions and diet are prepared in the same manner as for the *Spodoptera exigua* bioassay. Fourth instar larvae are used, and mortality is recorded after eight days.

*B. thuringiensis* PS81F, NRRL B-18424, and mutants thereof, can be cultured using standard known media and fermentation techniques. Upon completion of the fermentation cycle, the bacteria can be harvested by first separating the *B.t.* spores and crystals from the fermentation broth by means well known in the art. The recovered *B.t.* spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art and are used with commercial strains of *B. thuringiensis* (HD-1) active against Lepidoptera, e.g., caterpillars. *B.t.* PS81F, and mutants thereof, can be used to control lepidopteran pests.

A subculture of *B.t.* PS81F and the *E. coli* host harboring the toxin gene of the invention, *E. coli* DH5(α), containing the plasmid pMYC386, was deposited in the permanent collection of the Northern Research Laboratory, U.S. Department of Agriculture, Peoria, Ill., USA on Oct. 7, 1988. The accession numbers are as follows:

*B.t.* PS81F—NRRL B-18424

*E. coli* (DH5α) (pMYC386)—NRRL B-18423

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

The toxin gene of the subject invention can be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of lepidopteran insects where they will proliferate and be ingested by the insects. The result is a control of the unwanted insects. Alternatively, the microbe hosting the toxin gene can be treated under conditions that prolong the activity of the toxin produced in the cell. The treated cell then can be applied to the environment of target pest(s). The resulting product retains the toxicity of the *B.t.* toxin.

Where the *B.t.* toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae. Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are available for introducing the *B.t.* gene expressing the toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger, particularly by using an active promoter, as well as by employing sequences, which enhance the stability of the messenger RNA. The initiation and translational termination region will involve stop codon(s), a terminator region, and optionally, a polyadenylation signal.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the Tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pRO1614, and the like. See for example, Olson et al., (1982) J. Bacteriol. 150:6069, and Bagdasarian et al., (1981) Gene 16:237, and U.S. Pat. Nos. 4,356,270, 4,362,817, and 4,371,625.

The *B.t.* gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the *B.t.* gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., and the like. Specific organisms include *Pseudomonas aeruginosa, Pseudomonas fluorescens, Saccharomyces cerevisiae, Bacillus thuringiensis, Escherichia coli, Bacillus subtilis*, and the like.

The cell will usually be intact and be substantially in the proliferative form when treated, rather than in a spore form, although in some instances spores may be employed.

Treatment of the microbial cell, e.g., a microbe containing the *B.t.* toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the *B.t.* insecticidal gene may be grown in any convenient nutrient medium, where the DNA construct provides a selective advantage, providing for a selective medium so that substantially all or all of the cells retain the *B.t.* gene. These cells may then be harvested in accordance with conventional ways. Alternatively, the cells can be treated prior to harvesting.

The *B.t.* cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the lepidopteran pest(s), e.g., plants, soil or water, by spraying, dusting, sprinkling, or the like.

Mutants of PS81F can be made by procedures well known in the art. For example, an asporogenous mutant can be obtained through ethylmethane sulfonate (EMS) mutagenesis of PS81F. The mutants can be made using ultraviolet light and nitrosoguanidine by procedures well known in the art.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing *B.t.* PS81F, NRRL B-18424

A subculture of *B.t.* PS81F, NRRL B-18424, or mutants thereof, can be used to inoculate the following medium, a peptone, glucose, salts medium.

| | |
|---|---|
| Bacto Peptone | 7.5 g/l |
| Glucose | 1.0 g/l |
| KH$_2$PO$_4$ | 3.4 g/l |
| H$_2$HPO$_4$ | 4.35 g/l |
| Salt Solution | 5.0 ml/l |
| CaCl$_2$ Solution | 5.0 ml/l |

-continued

| | |
|---|---|
| Salts Solution (100 ml) | |
| MgSO$_4$.7H$_2$O | 2.46 g |
| MnSO$_4$.H$_2$O | 0.04 g |
| ZnSO$_4$.7H$_2$O | 0.28 g |
| FeSO$_4$.7H$_2$O | 0.40 g |
| CaCl$_2$ Solution (100 ml) | |
| CaCl$_2$.2H$_2$O | 3.66 g |
| pH 7.2 | |

The salts solution and CaCl$_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The *B.t.* spores and/or crystals, obtained in the above fermentation, can be isolated by procedures well known in the art. A frequently-used procedure is to subject the harvested fermentation broth to separation techniques, e.g., centrifugation.

EXAMPLE 2

Cloning of Novel Toxin Gene and Transformation into *Escherichia coli*

Total cellular DNA was prepared by growing the cells of *B. thuringiensis* HD-1 and the novel *B.t.* PS81F to a low optical density (OD$_{600}$=1.0) and recovering the cells by centrifugation. The cells were protoplasted in TES buffer (30 mM Tris-Cl, 10 mM EDTA, 50 mM NaCl, pH=8.0) containing 20% sucrose and 50 mg/ml lysozyme. The protoplasts were lysed by addition of SDS to a final concentration of 4%. The cellular material was precipitated overnight at 4° C. in 100 mM final concentration neutral potassium chloride. The supernate was extracted twice with phenol/chloroform (1:1). The DNA was precipitated in ethanol and purified by isopycnic banding on a cesium chloride gradient.

Total cellular DNA from each (PS81F and HD-1) was digested with EcoRI and separated by electrophoresis on a 0.8% Agarose-TAE-buffered gel. A Southern blot of the gel was probed with the NsiI to NsiI fragment of the toxin gene contained in plasmid pM3,130-7 of NRRL B-18332 and the NsiI to KpnI fragment of the "4.5 Kb class" toxin gene (Kronstad and Whitely [1986] Gene USA 43:29–40). These two fragments were combined and used as the probe. Results show that hybridizing fragments of PS81F are distinct from those of HD-1. Specifically, a 3.5 Kb hybridizing band in PS81F was detected instead of the 300 bp larger 3.8 Kb hybridizing band seen in HD-1.

Two hundred micrograms of PS81F total cellular DNA was digested with EcoRI and separated by electrophoresis on a preparative 0.8% Agarose-TAE gel. The 3.0 Kb to 4.0 Kb region of the gel was cut out and the DNA from it was electroeluted and concentrated using an ELUTIP™-d (Schleicher and Schuell, Keene, N.H.) ion exchange column. The isolated EcoRI fragments were ligated to LAMBDA ZAP™ EcoRI arms (Stratagene Cloning Systems, La Jolla, Calif.) and packaged using GIGAPACK GOLD™ extracts. The packaged recombinant phage were plated with *E. coli* strain BB4 (Stratagene) to give high plaque density. The plaques were screened by standard nucleic acid hybridization procedure with radiolabeled probe. The plaques that hybridized were purified and rescreened at a lower plaque density. The resulting purified phage were grown with R408 M13 helper phage (Stratagene) and the recombinant BLUESCRIPT™ (Stratagene) plasmid was automatically excised and packaged. The "phagemid" was re-infected in XL1-Blue *E. coli* cells (Stratagene) as part of the automatic excision process. The infected XL1-Blue cells were screened for ampicillin resistance and the resulting colonies were analyzed by standard miniprep procedure to find the desired plasmid. The plasmid, designated pM5,31-1, contained an approximate 3.5 Kb EcoRI insert and was sequenced using Stratagene's T7 and T3 primers plus a set of existing *B.t.* endotoxin oligonucleotide primers. About 1.7 Kb of the toxin gene was sequenced and data analysis comparing PS81F to other cloned *B.t.* endotoxin genes showed that the PS81F sequence was unique. A synthetic oligonucleotide (GCTGAAGAACTTC-CTATTCGTGGTGGTGAGC; SEQ ID NO: 4) was constructed to one of the regions in the PS81F sequence that was least homologous relative to other existing *B.t.* endotoxin genes.

Figure 2C:
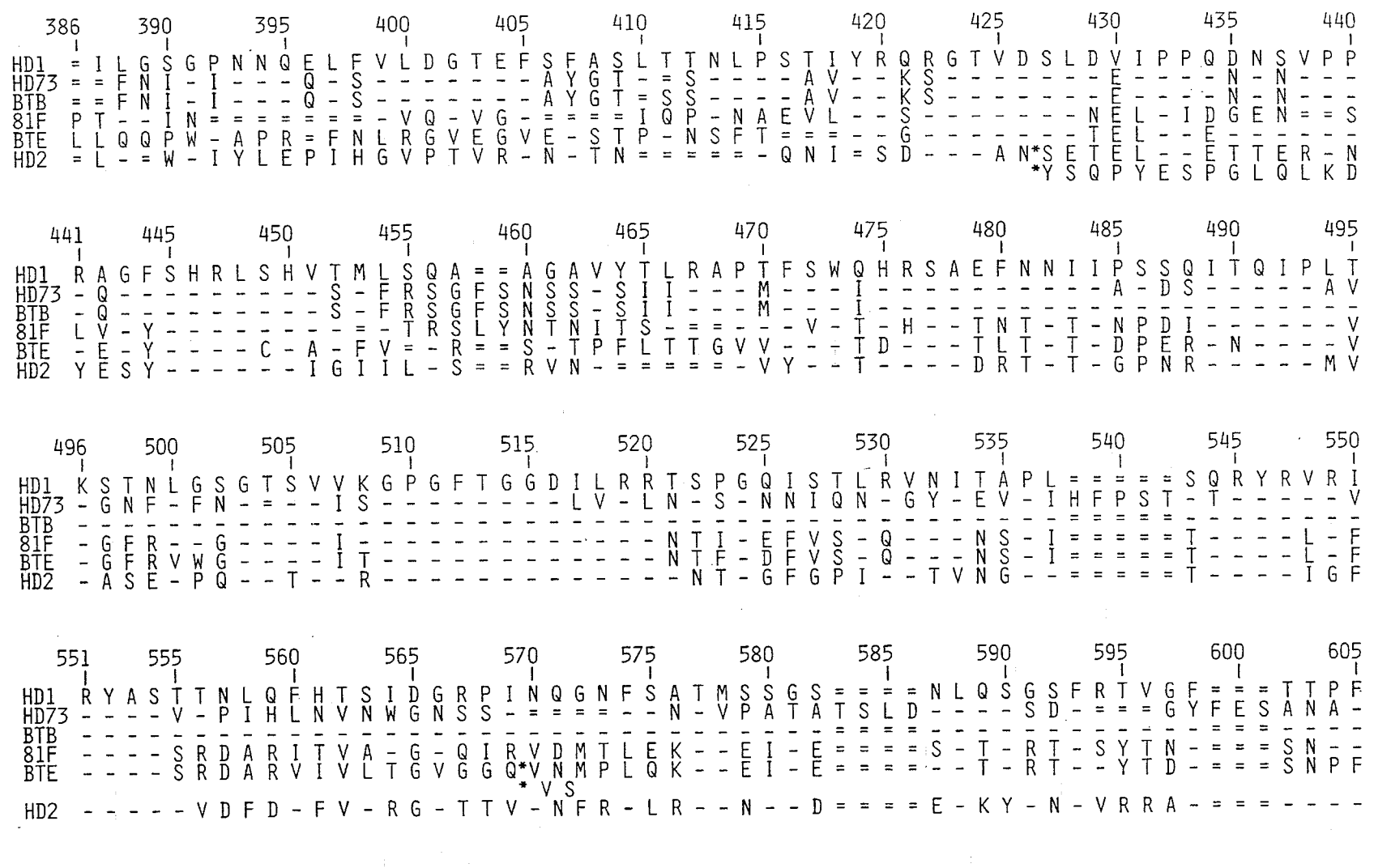

Total cellular DNA partially digested with Sau3A and fractionated by electrophoresis into a mixture of 9–23 Kb fragments on a 0.6% agarose TAE gel was ligated into LAMBDA DASH™ (Stratagene). The packaged phage were plated out with P2392 *E. coli* cells (Stratagene) at a high titer and screened using the radiolabeled synthetic oligonucleotide supra as a nucleic acid hybridization probe. Hybridizing plaques were rescreened at a lower plaque density. A purified hybridizing plaque was used to infect P2392 *E. coli* cells in liquid culture for preparation of phage for DNA isolation. DNA was isolated by standard procedures. Preparative amounts of recombinant phage DNA were digested with SalI (to release the inserted DNA from lambda arms) and separated by electrophoresis on a 0.6% Agarose-TAE gel. The large fragments (electroeluted and concentrated as described above) were ligated to an XhoI digested and phosphatased BLUESCRIPT™ plasmid. The ligation was transformed into *E. coli* DH5($\alpha$) competent cells (BRL) and plated on LB agar containing ampicillin, isopropyl-($\beta$)-D-thiogalactoside (IPTG) and 5-bromo-4-chloro-3-indolyl-($\beta$)-D-galactoside (XGAL). White colonies (with insertions in the ($\beta$)-galactosidase gene of pBluescript) were subjected to standard miniprep procedures to isolate the plasmid, designated pMI,43-24. The full length toxin gene was sequenced by using oligonucleotide primers made to the "4.3 Kb class" toxin gene and by "walking" with primers made to the sequence of PS81F. Data analysis comparing the deduced PS81F amino acid sequence to the sequences of five other endotoxins shows PS81F to be unique (FIG. 2).

The plasmid pM1,43-24 contains about 18 Kb of PS81F DNA including the 3.518 Kb which codes for the 133,266 dalton endotoxin. The plasmid was reduced in size by cutting out approximately 13 Kb of non-coding DNA, ligating the ends, transforming DH5($\alpha$) and plating on LB agar containing ampicillin. The resulting colonies were analyzed by standard miniprep procedures to isolate plasmids that were reduced in size. The desired plasmid, pMYC386, contains the coding sequence of the PS81F toxin gene, which could be excised as an SaeI to ApaI 4.5 Kb fragment.

The above cloning procedures were conducted using standard procedures unless otherwise noted.

The various methods employed in the preparation of the plasmids and transformation of host organisms are well known in the art. Also, methods for the use of lambda bacteriophage as a cloning vehicle, i.e., the preparation of lambda DNA, in vitro packaging, and transfection of recombinant DNA, are well known in the art. These procedures are all described in Maniatis, T., Fritsch, E. F., and Sambrook, J. (1982) *Molecular Cloning: A Laboratory Manual,* Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

The restriction enzymes disclosed herein can be purchased from Bethesda Research Laboratories, Gaithersburg, Md., or New England Biolabs, Beverly, Mass. The enzymes are used according to the instructions provided by the supplier.

Plasmid pMYC386 containing the *B.t.* toxin gene, can be removed from the transformed host microbe by use of standard well-known procedures. For example, *E. coli* NRRL B-18423 can be subjected to cleared lysate isopycnic density gradient procedures, and the like, to recover pMYC386.

Data from standard insect tests show that novel *B.t.* PS81F is active against diamondback moth, *Spodoptera exigua,* Western spruce budworm, and *T. ni.*

EXAMPLE 3

Insertion of Toxin Gene Into Plants

The novel gene coding for the novel insecticidal toxin, as disclosed herein, can be inserted into plant cells using the Ti plasmid from *Agrobacter tumefaciens.* Plant cells can then be caused to regenerate into plants (Zambryski, P., Joos, H., Gentello, C., Leemans, J., Van Montague, M. and Schell, J [1983] Cell 32:1033–1043). A particularly useful vector in this regard is pEND4K (Klee, H. J., Yanofsky, M. F. and Nester, E. W. [1985] Bio/Technology 3:637–642). This plasmid can replicate both in plant cells and in bacteria and has multiple cloning sites for passenger genes. The toxin gene, for example, can be inserted into the BamHI site of pEND4K, propagated in *E. coli,* and transformed into appropriate plant cells.

EXAMPLE 4

Cloning of Novel *B. thuringiensis* Gene Into Baculoviruses

The novel gene of the invention can be cloned into baculoviruses such as *Autographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miller, L. K. [1984] Mol. Cell. Biol. 4:399–406), and pAC380, described by Smith et al. (Smith, G. E., Summers, M. D. and Fraser, M. J. [1983] Mol Cell. Biol. 3:2156–2165). The gene coding for the novel protein toxin of the invention can be modified with BamHI linkers at appropriate regions both upstream and downstream from the coding region and inserted into the passenger site of one of the AcNPV vectors.

As disclosed previously, the nucleotide sequence encoding the novel *B.t.* toxin gene is shown in SEQ ID NOS. 1 and 2. The deduced amino acid sequence is shown in SEQ ID NOS. 1 and 3.

It is well known in the art that the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| | | | |
|---|---|---|---|
| Phenylalanine (Phe) | TTK | Histidine (His) | CAK |
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3-letter deoxynucleotide triplet corresponds to a trinucleotide of mRNA, having a 5'-end on the left and a 3'-end on the right. All DNA sequences given herein are those of the strand whose sequence correspond to the mRNA sequence, with thymine substituted for uracil. The letters stand for the purine or pyrimidine bases forming the deoxynucleotide sequence.

A=adenine
G=guanine
C=cytosine
T=thymine
X=T or C if Y is A or G
X=C if Y is C or T
Y=A, G, C or T if X is C
Y=A or G if X is T
W=C or A if Z is A or G
W—C if Z is C or T
Z=A, G, C or T if W is C
Z=A or G if W is A
QR=TC if S is A, G, C or T; alternatively QR=AG if S is T or C
J=A or G
K=T or C
L=A, T, C or G
M=A, C or T The above shows that the novel amino acid sequence of the *B.t.* toxin can be prepared by equivalent nucleotide sequences encoding the same amino acid sequence of the protein. Accordingly, the subject invention includes such equivalent nucleotide sequences. In addition it has been shown that proteins of identified structure and function may be constructed by changing the amino acid sequence if such changes do not alter the protein secondary structure (Kaiser, E. T. and Kezdy, F. J. [1984] Science 223:249–255). Thus, the subject invention includes mutants of the amino acid sequence depicted herein which do not alter the protein secondary structure, or if the structure is altered, the biological activity is retained to some degree.

We claim:

1. A purified toxin active against lepidopteran insects wherein said toxin has an amino add sequence shown in SEQ ID NO. 3.

2. A purified toxin active against lepidopteran insects wherein said toxin comprises an insecticidal portion of the full-length amino acid sequence shown in SEQ ID NO. 3.

3. The purified toxin, according to claim 2, wherein said toxin consists of the full-length amino acid sequence shown in SEQ ID NO. 3.

* * * * *

UNITED STATES PATENT AND TRADEMARK OFFICE
CERTIFICATE OF CORRECTION

PATENT NO. : 5,521,286
DATED : May 28, 1996
INVENTOR(S) : Jewel Payne; August J. Sick It is certified that error appears in the above-indentified patent and that said Letters Patent is hereby corrected as shown below:

Column 7, Line 64: "$H_2HPO_4$" should read --$K_2HPO_4$--.

Column 8, Line 34: "and. 50 mg/ml" should read --and 50 mg/ml--.

Signed and Sealed this

Eighth Day of October, 1996

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 3513 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..3513

( x i ) SEQUENCE DESCRIPTION: SEQ ID NO:1:

```
ATG  GAG  ATA  GTG  AAT  AAT  CAG  AAT  CAA  TGC  GTG  CCT  TAT  AAT  TGT  TTA         48
Met  Glu  Ile  Val  Asn  Asn  Gln  Asn  Gln  Cys  Val  Pro  Tyr  Asn  Cys  Leu
 1              5                        10                       15

AAT  AAT  CCT  GAA  AAT  GAG  ATA  TTA  GAT  ATT  GAA  AGG  TCA  AAT  AGT  ACT         96
Asn  Asn  Pro  Glu  Asn  Glu  Ile  Leu  Asp  Ile  Glu  Arg  Ser  Asn  Ser  Thr
               20                       25                       30

GTA  GCA  ACA  AAC  ATC  GCC  TTG  GAG  ATT  AGT  CGT  CTG  CTC  GCT  TCC  GCA        144
Val  Ala  Thr  Asn  Ile  Ala  Leu  Glu  Ile  Ser  Arg  Leu  Leu  Ala  Ser  Ala
          35                        40                       45

ACT  CCA  ATA  GGG  GGG  ATT  TTA  TTA  GGA  TTG  TTT  GAT  GCA  ATA  TGG  GGG        192
Thr  Pro  Ile  Gly  Gly  Ile  Leu  Leu  Gly  Leu  Phe  Asp  Ala  Ile  Trp  Gly
          50                        55                       60
```

| | | | | | | | | | | | | | | | | |
|---|---|---|---|---|---|---|---|---|---|---|---|---|---|---|---|---|
| TCT | ATA | GGC | CCT | TCA | CAA | TGG | GAT | TTA | TTT | TTA | GAG | CAA | ATT | GAG | CTA | 240 |
| Ser 65 | Ile | Gly | Pro | Ser 70 | Gln | Trp | Asp | Leu | Phe 75 | Leu | Glu | Gln | Ile | Glu | Leu 80 | |
| TTG | ATT | GAC | CAA | AAA | ATA | GAG | GAA | TTC | GCT | AGA | AAC | CAG | GCA | ATT | TCT | 288 |
| Leu | Ile | Asp | Gln | Lys 85 | Ile | Glu | Glu | Phe | Ala 90 | Arg | Asn | Gln | Ala | Ile 95 | Ser | |
| AGA | TTA | GAA | GGG | ATA | AGC | AGT | CTG | TAC | GGA | ATT | TAT | ACA | GAA | GCT | TTT | 336 |
| Arg | Leu | Glu | Gly 100 | Ile | Ser | Ser | Leu | Tyr 105 | Gly | Ile | Tyr | Thr | Glu 110 | Ala | Phe | |
| AGA | GAG | TGG | GAA | GCA | GAT | CCT | ACT | AAT | CCA | GCA | TTA | AAA | GAA | GAG | ATG | 384 |
| Arg | Glu | Trp 115 | Glu | Ala | Asp | Pro | Thr 120 | Asn | Pro | Ala | Leu | Lys 125 | Glu | Glu | Met | |
| CGT | ACT | CAA | TTT | AAT | GAC | ATG | AAC | AGT | ATT | CTT | GTA | ACA | GCT | ATT | CCT | 432 |
| Arg | Thr 130 | Gln | Phe | Asn | Asp | Met 135 | Asn | Ser | Ile | Leu | Val 140 | Thr | Ala | Ile | Pro | |
| CTT | TTT | TCA | GTT | CAA | AAT | TAT | CAA | GTC | CCA | TTT | TTA | TCA | GTA | TAT | GTT | 480 |
| Leu 145 | Phe | Ser | Val | Gln | Asn 150 | Tyr | Gln | Val | Pro | Phe 155 | Leu | Ser | Val | Tyr | Val 160 | |
| CAA | GCT | GCA | AAT | TTA | CAT | TTA | TCG | GTT | TTG | AGA | GAT | GTT | TCA | GTG | TTT | 528 |
| Gln | Ala | Ala | Asn | Leu 165 | His | Leu | Ser | Val | Leu 170 | Arg | Asp | Val | Ser | Val 175 | Phe | |
| GGG | CAG | GCT | TGG | GGA | TTT | GAT | ATA | GCA | ACA | ATA | AAT | AGT | CGT | TAT | AAT | 576 |
| Gly | Gln | Ala | Trp 180 | Gly | Phe | Asp | Ile | Ala 185 | Thr | Ile | Asn | Ser | Arg 190 | Tyr | Asn | |
| GAT | CTG | ACT | AGA | CTT | ATT | CCT | ATA | TAT | ACA | GAT | TAT | GCT | GTA | CGC | TGG | 624 |
| Asp | Leu | Thr | Arg 195 | Leu | Ile | Pro | Ile | Tyr 200 | Thr | Asp | Tyr | Ala | Val 205 | Arg | Trp | |
| TAC | AAT | ACG | GGA | TTA | GAT | CGC | TTA | CCA | CGA | ACT | GGT | GGG | CTG | CGA | AAC | 672 |
| Tyr | Asn | Thr | Gly | Leu 210 | Asp | Arg | Leu | Pro | Arg 215 | Thr | Gly | Gly | Leu | Arg 220 | Asn | |
| TGG | GCA | AGA | TTT | AAT | CAG | TTT | AGA | AGA | GAG | TTA | ACA | ATA | TCA | GTA | TTA | 720 |
| Trp 225 | Ala | Arg | Phe | Asn | Gln 230 | Phe | Arg | Arg | Glu | Leu 235 | Thr | Ile | Ser | Val | Leu 240 | |
| GAT | ATT | ATT | TCT | TTT | TTC | AGA | AAT | TAC | GAT | TCT | AGA | TTA | TAT | CCA | ATT | 768 |
| Asp | Ile | Ile | Ser | Phe 245 | Phe | Arg | Asn | Tyr | Asp 250 | Ser | Arg | Leu | Tyr | Pro 255 | Ile | |
| CCA | ACA | AGC | TCC | CAA | TTA | ACG | CGG | GAA | GTA | TAT | ACA | GAT | CCG | GTA | ATT | 816 |
| Pro | Thr | Ser | Ser 260 | Gln | Leu | Thr | Arg | Glu 265 | Val | Tyr | Thr | Asp | Pro 270 | Val | Ile | |
| AAT | ATA | ACT | GAC | TAT | AGA | GTT | GGC | CCC | AGC | TTC | GAG | AAT | ATT | GAG | AAC | 864 |
| Asn | Ile | Thr 275 | Asp | Tyr | Arg | Val | Gly 280 | Pro | Ser | Phe | Glu | Asn 285 | Ile | Glu | Asn | |
| TCA | GCC | ATT | AGA | AGC | CCC | CAC | CTT | ATG | GAC | TTC | TTA | AAT | AAT | TTG | ACC | 912 |
| Ser | Ala | Ile | Arg 290 | Ser | Pro | His | Leu | Met 295 | Asp | Phe | Leu | Asn | Asn 300 | Leu | Thr | |
| ATT | GAT | ACG | GAT | TTG | ATT | AGA | GGT | GTT | CAC | TAT | TGG | GCA | GGG | CAT | CGT | 960 |
| Ile | Asp | Thr | Asp 305 | Leu | Ile | Arg | Gly | Val 310 | His | Tyr | Trp | Ala | Gly 315 | His | Arg 320 | |
| GTA | ACT | TCT | CAT | TTT | ACA | GGT | AGT | TCT | CAA | GTG | ATA | ACA | ACC | CCT | CAA | 1008 |
| Val | Thr | Ser | His | Phe 325 | Thr | Gly | Ser | Ser | Gln 330 | Val | Ile | Thr | Thr | Pro 335 | Gln | |
| TAT | GGG | ATA | ACC | GCA | AAT | GCG | GAA | CCA | AGA | CGA | ACT | ATT | GCT | CCT | AGT | 1056 |
| Tyr | Gly | Ile | Thr 340 | Ala | Asn | Ala | Glu | Pro 345 | Arg | Arg | Thr | Ile | Ala 350 | Pro | Ser | |
| ACT | TTT | CCA | GGT | CTT | AAC | CTA | TTT | TAT | AGA | ACA | TTA | TCA | AAT | CCT | TTC | 1104 |
| Thr | Phe | Pro 355 | Gly | Leu | Asn | Leu | Phe 360 | Tyr | Arg | Thr | Leu | Ser 365 | Asn | Pro | Phe | |
| TTC | CGA | AGA | TCA | GAA | AAT | ATT | ACT | CCT | ACC | TTA | GGG | ATA | AAT | GTA | GTA | 1152 |
| Phe | Arg | Arg 370 | Ser | Glu | Asn | Ile | Thr 375 | Pro | Thr | Leu | Gly | Ile 380 | Asn | Val | Val | |

| | | | | | | | | | | | | | | | | |
|---|---|---|---|---|---|---|---|---|---|---|---|---|---|---|---|---|
| CAG | GGA | GTA | GGG | TTC | ATT | CAA | CCA | AAT | AAT | GCT | GAA | GTT | CTA | TAT | AGA | 1200 |
| Gln | Gly | Val | Gly | Phe | Ile | Gln | Pro | Asn | Asn | Ala | Glu | Val | Leu | Tyr | Arg | |
| 385 | | | | 390 | | | | | 395 | | | | | | 400 | |
| AGT | AGG | GGG | ACA | GTA | GAT | TCT | CTT | AAT | GAG | TTA | CCA | ATT | GAT | GGT | GAG | 1248 |
| Ser | Arg | Gly | Thr | Val | Asp | Ser | Leu | Asn | Glu | Leu | Pro | Ile | Asp | Gly | Glu | |
| | | | | 405 | | | | | 410 | | | | | 415 | | |
| AAT | TCA | TTA | GTT | GGA | TAT | AGT | CAT | CGA | TTA | AGT | CAT | GTT | ACA | CTA | ACC | 1296 |
| Asn | Ser | Leu | Val | Gly | Tyr | Ser | His | Arg | Leu | Ser | His | Val | Thr | Leu | Thr | |
| | | | 420 | | | | | 425 | | | | | 430 | | | |
| AGG | TCG | TTA | TAT | AAT | ACT | AAT | ATA | ACT | AGC | CTG | CCA | ACA | TTT | GTT | TGG | 1344 |
| Arg | Ser | Leu | Tyr | Asn | Thr | Asn | Ile | Thr | Ser | Leu | Pro | Thr | Phe | Val | Trp | |
| | | | 435 | | | | | 440 | | | | | 445 | | | |
| ACA | CAT | CAC | AGT | GCT | ACT | AAT | ACA | AAT | ACA | ATT | AAT | CCA | GAT | ATT | ATT | 1392 |
| Thr | His | His | Ser | Ala | Thr | Asn | Thr | Asn | Thr | Ile | Asn | Pro | Asp | Ile | Ile | |
| | | 450 | | | | | 455 | | | | | 460 | | | | |
| ACA | CAA | ATA | CCT | TTA | GTG | AAA | GGA | TTT | AGA | CTT | GGT | GGT | GGC | ACC | TCT | 1440 |
| Thr | Gln | Ile | Pro | Leu | Val | Lys | Gly | Phe | Arg | Leu | Gly | Gly | Gly | Thr | Ser | |
| 465 | | | | | 470 | | | | | 475 | | | | | 480 | |
| GTC | ATT | AAA | GGA | CCA | GGA | TTT | ACA | GGA | GGG | GAT | ATC | CTT | CGA | AGA | AAT | 1488 |
| Val | Ile | Lys | Gly | Pro | Gly | Phe | Thr | Gly | Gly | Asp | Ile | Leu | Arg | Arg | Asn | |
| | | | | 485 | | | | | 490 | | | | | 495 | | |
| ACC | ATT | GGT | GAG | TTT | GTG | TCT | TTA | CAA | GTC | AAT | ATT | AAC | TCA | CCA | ATT | 1536 |
| Thr | Ile | Gly | Glu | Phe | Val | Ser | Leu | Gln | Val | Asn | Ile | Asn | Ser | Pro | Ile | |
| | | | | 500 | | | | | 505 | | | | | 510 | | |
| ACC | CAA | AGA | TAC | CGT | TTA | AGA | TTT | CGT | TAT | GCT | TCC | AGT | AGG | GAT | GCA | 1584 |
| Thr | Gln | Arg | Tyr | Arg | Leu | Arg | Phe | Arg | Tyr | Ala | Ser | Ser | Arg | Asp | Ala | |
| | | 515 | | | | | 520 | | | | | 525 | | | | |
| CGA | ATT | ACT | GTA | GCG | ATA | GGA | GGA | CAA | ATT | AGA | GTA | GAT | ATG | ACC | CTT | 1632 |
| Arg | Ile | Thr | Val | Ala | Ile | Gly | Gly | Gln | Ile | Arg | Val | Asp | Met | Thr | Leu | |
| | | 530 | | | | | 535 | | | | | 540 | | | | |
| GAA | AAA | ACC | ATG | GAA | ATT | GGG | GAG | AGC | TTA | ACA | TCT | AGA | ACA | TTT | AGC | 1680 |
| Glu | Lys | Thr | Met | Glu | Ile | Gly | Glu | Ser | Leu | Thr | Ser | Arg | Thr | Phe | Ser | |
| 545 | | | | | 550 | | | | | 555 | | | | | 560 | |
| TAT | ACC | AAT | TTT | AGT | AAT | CCT | TTT | TCA | TTT | AGG | GCT | AAT | CCA | GAT | ATA | 1728 |
| Tyr | Thr | Asn | Phe | Ser | Asn | Pro | Phe | Ser | Phe | Arg | Ala | Asn | Pro | Asp | Ile | |
| | | | | 565 | | | | | 570 | | | | | 575 | | |
| ATT | AGA | ATA | GCT | GAA | GAA | CTT | CCT | ATT | CGT | GGT | GGT | GAG | CTT | TAT | ATA | 1776 |
| Ile | Arg | Ile | Ala | Glu | Glu | Leu | Pro | Ile | Arg | Gly | Gly | Glu | Leu | Tyr | Ile | |
| | | | 580 | | | | | 585 | | | | | 590 | | | |
| GAT | AAA | ATT | GAA | CTT | ATT | CTA | GCA | GAT | GCA | ACA | TTT | GAA | GAA | GAA | TAT | 1824 |
| Asp | Lys | Ile | Glu | Leu | Ile | Leu | Ala | Asp | Ala | Thr | Phe | Glu | Glu | Glu | Tyr | |
| | 595 | | | | | 600 | | | | | 605 | | | | | |
| GAT | TTG | GAA | AGA | GCA | CAG | AAG | GCG | GTG | AAT | GCC | CTG | TTT | ACT | TCT | ACA | 1872 |
| Asp | Leu | Glu | Arg | Ala | Gln | Lys | Ala | Val | Asn | Ala | Leu | Phe | Thr | Ser | Thr | |
| | 610 | | | | | 615 | | | | | 620 | | | | | |
| AAT | CAA | CTA | GGG | CTA | AAA | ACA | GAT | GTG | ACG | GAT | TAT | CAT | ATT | GAT | CAA | 1920 |
| Asn | Gln | Leu | Gly | Leu | Lys | Thr | Asp | Val | Thr | Asp | Tyr | His | Ile | Asp | Gln | |
| 625 | | | | | 630 | | | | | 635 | | | | | 640 | |
| GTT | TCC | AAT | TTA | GTT | GAG | TGT | TTA | TCG | GAT | GAA | TTT | TGT | CTG | GAT | GAA | 1968 |
| Val | Ser | Asn | Leu | Val | Glu | Cys | Leu | Ser | Asp | Glu | Phe | Cys | Leu | Asp | Glu | |
| | | | | 645 | | | | | 650 | | | | | 655 | | |
| AAG | AGA | GAA | TTA | TCC | GAG | AAA | GTC | AAA | CAT | GCG | AAG | CGA | CTC | AGT | GAT | 2016 |
| Lys | Arg | Glu | Leu | Ser | Glu | Lys | Val | Lys | His | Ala | Lys | Arg | Leu | Ser | Asp | |
| | | | | 660 | | | | | 665 | | | | | 670 | | |
| GAA | CGG | AAT | TTA | CTT | CAA | GAT | CCA | AAC | TTC | AGA | GGG | ATC | AAT | AGG | CAA | 2064 |
| Glu | Arg | Asn | Leu | Leu | Gln | Asp | Pro | Asn | Phe | Arg | Gly | Ile | Asn | Arg | Gln | |
| | | | 675 | | | | | 680 | | | | | 685 | | | |
| CCA | GAC | CGT | GGC | TGG | AGA | GGA | AGC | ACG | GAT | ATT | ACT | ATC | CAA | GGT | GGA | 2112 |
| Pro | Asp | Arg | Gly | Trp | Arg | Gly | Ser | Thr | Asp | Ile | Thr | Ile | Gln | Gly | Gly | |
| | 690 | | | | | 695 | | | | | 700 | | | | | |

```
GAT GAC GTA TTC AAA GAG AAT TAC GTC ACA TTA CCG GGT ACC TTT GAT    2160
Asp Asp Val Phe Lys Glu Asn Tyr Val Thr Leu Pro Gly Thr Phe Asp
705             710             715             720

GAG TGC TAT CCA ACG TAT TTA TAT CAA AAA ATA GAT GAG TCG AAG TTA    2208
Glu Cys Tyr Pro Thr Tyr Leu Tyr Gln Lys Ile Asp Glu Ser Lys Leu
            725             730             735

AAA GCT TAT ACC CGC TAT GAA TTA AGA GGG TAT ATC GAG GAT AGT CAA    2256
Lys Ala Tyr Thr Arg Tyr Glu Leu Arg Gly Tyr Ile Glu Asp Ser Gln
            740             745             750

GAC TTA GAA ATC TAT TTA ATT CGC TAC AAT GCA AAA CAC GAG ACA GTA    2304
Asp Leu Glu Ile Tyr Leu Ile Arg Tyr Asn Ala Lys His Glu Thr Val
        755             760             765

AAC GTG CCA GGT ACG GGT TCC TTA TGG CCG CTT TCA GCC CAA AGT CCA    2352
Asn Val Pro Gly Thr Gly Ser Leu Trp Pro Leu Ser Ala Gln Ser Pro
770             775             780

ATC GGA AAG TGT GGA GAA CCG AAT CGA TGC GCG CCA CAC CTT GAA TGG    2400
Ile Gly Lys Cys Gly Glu Pro Asn Arg Cys Ala Pro His Leu Glu Trp
785             790             795             800

AAT CCT AAT CTA GAT TGC TCC TGC AGA GAC GGG GAA AAA TGT GCC CAT    2448
Asn Pro Asn Leu Asp Cys Ser Cys Arg Asp Gly Glu Lys Cys Ala His
                805             810             815

CAT TCC CAT CAT TTC TCC TTG GAC ATT GAT GTT GGA TGT ACA GAC TTA    2496
His Ser His His Phe Ser Leu Asp Ile Asp Val Gly Cys Thr Asp Leu
            820             825             830

AAT GAG GAC TTA GGT GTA TGG GTG ATA TTC AAG ATT AAG ACA CAA GAT    2544
Asn Glu Asp Leu Gly Val Trp Val Ile Phe Lys Ile Lys Thr Gln Asp
        835             840             845

GGC TAT GCA AGA CTA GGA AAT CTA GAG TTT CTC GAA GAG AAA CCA CTA    2592
Gly Tyr Ala Arg Leu Gly Asn Leu Glu Phe Leu Glu Glu Lys Pro Leu
850             855             860

TTA GGG GAA GCA CTA GCT CGT GTG AAA AGA GCG GAG AAA AAA TGG AGA    2640
Leu Gly Glu Ala Leu Ala Arg Val Lys Arg Ala Glu Lys Lys Trp Arg
865             870             875             880

GAC AAA TGC GAA AAA TTG GAA TGG GAA ACA AAT ATT GTT TAT AAA GAG    2688
Asp Lys Cys Glu Lys Leu Glu Trp Glu Thr Asn Ile Val Tyr Lys Glu
            885             890             895

GCA AAA GAA TCT GTA GAT GCT TTA TTT GTA AAC TCT CAA TAT GAT AGA    2736
Ala Lys Glu Ser Val Asp Ala Leu Phe Val Asn Ser Gln Tyr Asp Arg
            900             905             910

TTA CAA GCG GAT ACG AAT ATC GCG ATG ATT CAT GCG GCA GAT AAA CGC    2784
Leu Gln Ala Asp Thr Asn Ile Ala Met Ile His Ala Ala Asp Lys Arg
        915             920             925

GTT CAT AGC ATT CGA GAA GCG TAT CTG CCA GAG CTG TCT GTG ATT CCG    2832
Val His Ser Ile Arg Glu Ala Tyr Leu Pro Glu Leu Ser Val Ile Pro
    930             935             940

GGT GTC AAT GCG GCT ATT TTT GAA GAA TTA GAA GGG CGT ATT TTC ACT    2880
Gly Val Asn Ala Ala Ile Phe Glu Glu Leu Glu Gly Arg Ile Phe Thr
945             950             955             960

GCA TTC TCC CTA TAT GAT GCG AGA AAT GTC ATT AAA AAT GGC GAT TTC    2928
Ala Phe Ser Leu Tyr Asp Ala Arg Asn Val Ile Lys Asn Gly Asp Phe
            965             970             975

AAT AAT GGC TTA TCA TGC TGG AAC GTG AAA GGG CAT GTA GAT GTA GAA    2976
Asn Asn Gly Leu Ser Cys Trp Asn Val Lys Gly His Val Asp Val Glu
        980             985             990

GAA CAG AAC AAC CAT CGT TCG GTC CTT GTT GTT CCA GAA TGG GAA GCA    3024
Glu Gln Asn Asn His Arg Ser Val Leu Val Val Pro Glu Trp Glu Ala
        995             1000            1005

GAA GTG TCA CAA GAA GTT CGT GTT TGT CCG GGT CGT GGC TAT ATC CTT    3072
Glu Val Ser Gln Glu Val Arg Val Cys Pro Gly Arg Gly Tyr Ile Leu
    1010            1015            1020
```

| | | | | | | | | | | | | | | | | |
|---|---|---|---|---|---|---|---|---|---|---|---|---|---|---|---|---|
| CGT | GTT | ACA | GCG | TAC | AAA | GAG | GGA | TAT | GGA | GAG | GGC | TGT | GTA | ACG | ATT | 3120 |
| Arg | Val | Thr | Ala | Tyr | Lys | Glu | Gly | Tyr | Gly | Glu | Gly | Cys | Val | Thr | Ile | |
| 1025 | | | | 1030 | | | | | 1035 | | | | | | 1040 | |
| CAT | GAG | ATC | GAA | GAC | AAT | ACA | GAC | GAA | CTG | AAA | TTC | AGC | AAC | TGT | GTA | 3168 |
| His | Glu | Ile | Glu | Asp | Asn | Thr | Asp | Glu | Leu | Lys | Phe | Ser | Asn | Cys | Val | |
| | | | | 1045 | | | | | 1050 | | | | | 1055 | | |
| GAA | GAG | GAA | GTA | TAT | CCA | AAC | AAC | ACG | GTA | ACG | TGT | AAT | AAT | TAT | ACT | 3216 |
| Glu | Glu | Glu | Val | Tyr | Pro | Asn | Asn | Thr | Val | Thr | Cys | Asn | Asn | Tyr | Thr | |
| | | | 1060 | | | | | 1065 | | | | | 1070 | | | |
| GCG | ACT | CAA | GAA | GAA | CAT | GAG | GGT | ACG | TAC | ACT | TCC | CGT | AAT | CGA | GGA | 3264 |
| Ala | Thr | Gln | Glu | Glu | His | Glu | Gly | Thr | Tyr | Thr | Ser | Arg | Asn | Arg | Gly | |
| | | | 1075 | | | | | 1080 | | | | | 1085 | | | |
| TAT | GAC | GAA | GCC | TAT | GAA | AGC | AAT | TCT | TCT | GTA | CAT | GCG | TCA | GTC | TAT | 3312 |
| Tyr | Asp | Glu | Ala | Tyr | Glu | Ser | Asn | Ser | Ser | Val | His | Ala | Ser | Val | Tyr | |
| | | 1090 | | | | 1095 | | | | | 1100 | | | | | |
| GAA | GAA | AAA | TCG | TAT | ACA | GAT | AGA | CGA | AGA | GAG | AAT | CCT | TGT | GAA | TCT | 3360 |
| Glu | Glu | Lys | Ser | Tyr | Thr | Asp | Arg | Arg | Arg | Glu | Asn | Pro | Cys | Glu | Ser | |
| 1105 | | | | | 1110 | | | | | 1115 | | | | | 1120 | |
| AAC | AGA | GGA | TAT | GGG | GAT | TAC | ACA | CCA | CTA | CCA | GCT | GGC | TAT | GTG | ACA | 3408 |
| Asn | Arg | Gly | Tyr | Gly | Asp | Tyr | Thr | Pro | Leu | Pro | Ala | Gly | Tyr | Val | Thr | |
| | | | | 1125 | | | | | 1130 | | | | | 1135 | | |
| AAA | GAA | TTA | GAG | TAC | TTC | CCA | GAA | ACC | GAT | AAG | GTA | TGG | ATT | GAG | ATC | 3456 |
| Lys | Glu | Leu | Glu | Tyr | Phe | Pro | Glu | Thr | Asp | Lys | Val | Trp | Ile | Glu | Ile | |
| | | | 1140 | | | | | 1145 | | | | | 1150 | | | |
| GGA | GAA | ACG | GAA | GGA | ACA | TTC | ATC | GTG | GAC | AGC | GTG | GAA | TTA | CTT | CTT | 3504 |
| Gly | Glu | Thr | Glu | Gly | Thr | Phe | Ile | Val | Asp | Ser | Val | Glu | Leu | Leu | Leu | |
| | | | 1155 | | | | | 1160 | | | | | 1165 | | | |
| ATG | GAG | GAA | | | | | | | | | | | | | | 3513 |
| Met | Glu | Glu | | | | | | | | | | | | | | |
| | | 1170 | | | | | | | | | | | | | | |

( 2 ) INFORMATION FOR SEQ ID NO:2:

( i ) SEQUENCE CHARACTERISTICS:
        ( A ) LENGTH: 1171 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Glu | Ile | Val | Asn | Asn | Gln | Asn | Gln | Cys | Val | Pro | Tyr | Asn | Cys | Leu |
| 1 | | | | 5 | | | | | 10 | | | | | 15 | |
| Asn | Asn | Pro | Glu | Asn | Glu | Ile | Leu | Asp | Ile | Glu | Arg | Ser | Asn | Ser | Thr |
| | | | 20 | | | | | 25 | | | | | 30 | | |
| Val | Ala | Thr | Asn | Ile | Ala | Leu | Glu | Ile | Ser | Arg | Leu | Leu | Ala | Ser | Ala |
| | | 35 | | | | | 40 | | | | | 45 | | | |
| Thr | Pro | Ile | Gly | Gly | Ile | Leu | Leu | Gly | Leu | Phe | Asp | Ala | Ile | Trp | Gly |
| | 50 | | | | | 55 | | | | | 60 | | | | |
| Ser | Ile | Gly | Pro | Ser | Gln | Trp | Asp | Leu | Phe | Leu | Glu | Gln | Ile | Glu | Leu |
| 65 | | | | | 70 | | | | | 75 | | | | | 80 |
| Leu | Ile | Asp | Gln | Lys | Ile | Glu | Glu | Phe | Ala | Arg | Asn | Gln | Ala | Ile | Ser |
| | | | | 85 | | | | | 90 | | | | | 95 | |
| Arg | Leu | Glu | Gly | Ile | Ser | Ser | Leu | Tyr | Gly | Ile | Tyr | Thr | Glu | Ala | Phe |
| | | | 100 | | | | | 105 | | | | | 110 | | |
| Arg | Glu | Trp | Glu | Ala | Asp | Pro | Thr | Asn | Pro | Ala | Leu | Lys | Glu | Glu | Met |
| | | | 115 | | | | | 120 | | | | | 125 | | |
| Arg | Thr | Gln | Phe | Asn | Asp | Met | Asn | Ser | Ile | Leu | Val | Thr | Ala | Ile | Pro |
| | | 130 | | | | | 135 | | | | | 140 | | | |

| | | | | | | | | | | | | | | | |
|---|---|---|---|---|---|---|---|---|---|---|---|---|---|---|---|
| Leu | Phe | Ser | Val | Gln | Asn | Tyr | Gln | Val | Pro | Phe | Leu | Ser | Val | Tyr | Val |
| 145 | | | | | 150 | | | | | 155 | | | | | 160 |
| Gln | Ala | Ala | Asn | Leu | His | Leu | Ser | Val | Leu | Arg | Asp | Val | Ser | Val | Phe |
| | | | | 165 | | | | | 170 | | | | 175 | | |
| Gly | Gln | Ala | Trp | Gly | Phe | Asp | Ile | Ala | Thr | Ile | Asn | Ser | Arg | Tyr | Asn |
| | | | 180 | | | | | 185 | | | | | 190 | | |
| Asp | Leu | Thr | Arg | Leu | Ile | Pro | Ile | Tyr | Thr | Asp | Tyr | Ala | Val | Arg | Trp |
| | | 195 | | | | | 200 | | | | | 205 | | | |
| Tyr | Asn | Thr | Gly | Leu | Asp | Arg | Leu | Pro | Arg | Thr | Gly | Gly | Leu | Arg | Asn |
| | 210 | | | | | 215 | | | | | 220 | | | | |
| Trp | Ala | Arg | Phe | Asn | Gln | Phe | Arg | Arg | Glu | Leu | Thr | Ile | Ser | Val | Leu |
| 225 | | | | | 230 | | | | | 235 | | | | | 240 |
| Asp | Ile | Ile | Ser | Phe | Phe | Arg | Asn | Tyr | Asp | Ser | Arg | Leu | Tyr | Pro | Ile |
| | | | | 245 | | | | | 250 | | | | | 255 | |
| Pro | Thr | Ser | Ser | Gln | Leu | Thr | Arg | Glu | Val | Tyr | Thr | Asp | Pro | Val | Ile |
| | | | 260 | | | | | 265 | | | | | 270 | | |
| Asn | Ile | Thr | Asp | Tyr | Arg | Val | Gly | Pro | Ser | Phe | Glu | Asn | Ile | Glu | Asn |
| | | 275 | | | | | 280 | | | | | 285 | | | |
| Ser | Ala | Ile | Arg | Ser | Pro | His | Leu | Met | Asp | Phe | Leu | Asn | Asn | Leu | Thr |
| | 290 | | | | | 295 | | | | | 300 | | | | |
| Ile | Asp | Thr | Asp | Leu | Ile | Arg | Gly | Val | His | Tyr | Trp | Ala | Gly | His | Arg |
| 305 | | | | | 310 | | | | | 315 | | | | | 320 |
| Val | Thr | Ser | His | Phe | Thr | Gly | Ser | Ser | Gln | Val | Ile | Thr | Thr | Pro | Gln |
| | | | | 325 | | | | | 330 | | | | | 335 | |
| Tyr | Gly | Ile | Thr | Ala | Asn | Ala | Glu | Pro | Arg | Arg | Thr | Ile | Ala | Pro | Ser |
| | | | 340 | | | | | 345 | | | | | 350 | | |
| Thr | Phe | Pro | Gly | Leu | Asn | Leu | Phe | Tyr | Arg | Thr | Leu | Ser | Asn | Pro | Phe |
| | | 355 | | | | | 360 | | | | | 365 | | | |
| Phe | Arg | Arg | Ser | Glu | Asn | Ile | Thr | Pro | Thr | Leu | Gly | Ile | Asn | Val | Val |
| | 370 | | | | | 375 | | | | | 380 | | | | |
| Gln | Gly | Val | Gly | Phe | Ile | Gln | Pro | Asn | Asn | Ala | Glu | Val | Leu | Tyr | Arg |
| 385 | | | | | 390 | | | | | 395 | | | | | 400 |
| Ser | Arg | Gly | Thr | Val | Asp | Ser | Leu | Asn | Glu | Leu | Pro | Ile | Asp | Gly | Glu |
| | | | | 405 | | | | | 410 | | | | | 415 | |
| Asn | Ser | Leu | Val | Gly | Tyr | Ser | His | Arg | Leu | Ser | His | Val | Thr | Leu | Thr |
| | | | 420 | | | | | 425 | | | | | 430 | | |
| Arg | Ser | Leu | Tyr | Asn | Thr | Asn | Ile | Thr | Ser | Leu | Pro | Thr | Phe | Val | Trp |
| | | 435 | | | | | 440 | | | | | 445 | | | |
| Thr | His | His | Ser | Ala | Thr | Asn | Thr | Asn | Thr | Ile | Asn | Pro | Asp | Ile | Ile |
| | 450 | | | | | 455 | | | | | 460 | | | | |
| Thr | Gln | Ile | Pro | Leu | Val | Lys | Gly | Phe | Arg | Leu | Gly | Gly | Gly | Thr | Ser |
| 465 | | | | | 470 | | | | | 475 | | | | | 480 |
| Val | Ile | Lys | Gly | Pro | Gly | Phe | Thr | Gly | Gly | Asp | Ile | Leu | Arg | Arg | Asn |
| | | | | 485 | | | | | 490 | | | | | 495 | |
| Thr | Ile | Gly | Glu | Phe | Val | Ser | Leu | Gln | Val | Asn | Ile | Asn | Ser | Pro | Ile |
| | | | 500 | | | | | 505 | | | | | 510 | | |
| Thr | Gln | Arg | Tyr | Arg | Leu | Arg | Phe | Arg | Tyr | Ala | Ser | Ser | Arg | Asp | Ala |
| | | 515 | | | | | 520 | | | | | 525 | | | |
| Arg | Ile | Thr | Val | Ala | Ile | Gly | Gly | Gln | Ile | Arg | Val | Asp | Met | Thr | Leu |
| | 530 | | | | | 535 | | | | | 540 | | | | |
| Glu | Lys | Thr | Met | Glu | Ile | Gly | Glu | Ser | Leu | Thr | Ser | Arg | Thr | Phe | Ser |
| 545 | | | | | 550 | | | | | 555 | | | | | 560 |
| Tyr | Thr | Asn | Phe | Ser | Asn | Pro | Phe | Ser | Phe | Arg | Ala | Asn | Pro | Asp | Ile |
| | | | | 565 | | | | | 570 | | | | | 575 | |

```
Ile Arg Ile Ala Glu Glu Leu Pro Ile Arg Gly Gly Glu Leu Tyr Ile
            580                 585                 590
Asp Lys Ile Glu Leu Ile Leu Ala Asp Ala Thr Phe Glu Glu Tyr
        595                 600                 605
Asp Leu Glu Arg Ala Gln Lys Ala Val Asn Ala Leu Phe Thr Ser Thr
        610                 615                 620
Asn Gln Leu Gly Leu Lys Thr Asp Val Thr Asp Tyr His Ile Asp Gln
625                 630                 635                 640
Val Ser Asn Leu Val Glu Cys Leu Ser Asp Glu Phe Cys Leu Asp Glu
                645                 650                 655
Lys Arg Glu Leu Ser Glu Lys Val Lys His Ala Lys Arg Leu Ser Asp
            660                 665                 670
Glu Arg Asn Leu Leu Gln Asp Pro Asn Phe Arg Gly Ile Asn Arg Gln
        675                 680                 685
Pro Asp Arg Gly Trp Arg Gly Ser Thr Asp Ile Thr Ile Gln Gly Gly
        690                 695                 700
Asp Asp Val Phe Lys Glu Asn Tyr Val Thr Leu Pro Gly Thr Phe Asp
705                 710                 715                 720
Glu Cys Tyr Pro Thr Tyr Leu Tyr Gln Lys Ile Asp Glu Ser Lys Leu
                725                 730                 735
Lys Ala Tyr Thr Arg Tyr Glu Leu Arg Gly Tyr Ile Glu Asp Ser Gln
            740                 745                 750
Asp Leu Glu Ile Tyr Leu Ile Arg Tyr Asn Ala Lys His Glu Thr Val
        755                 760                 765
Asn Val Pro Gly Thr Gly Ser Leu Trp Pro Leu Ser Ala Gln Ser Pro
770                 775                 780
Ile Gly Lys Cys Gly Glu Pro Asn Arg Cys Ala Pro His Leu Glu Trp
785                 790                 795                 800
Asn Pro Asn Leu Asp Cys Ser Cys Arg Asp Gly Glu Lys Cys Ala His
                805                 810                 815
His Ser His His Phe Ser Leu Asp Ile Asp Val Gly Cys Thr Asp Leu
            820                 825                 830
Asn Glu Asp Leu Gly Val Trp Val Ile Phe Lys Ile Lys Thr Gln Asp
        835                 840                 845
Gly Tyr Ala Arg Leu Gly Asn Leu Glu Phe Leu Glu Glu Lys Pro Leu
850                 855                 860
Leu Gly Glu Ala Leu Ala Arg Val Lys Arg Ala Glu Lys Lys Trp Arg
865                 870                 875                 880
Asp Lys Cys Glu Lys Leu Glu Trp Glu Thr Asn Ile Val Tyr Lys Glu
                885                 890                 895
Ala Lys Glu Ser Val Asp Ala Leu Phe Val Asn Ser Gln Tyr Asp Arg
            900                 905                 910
Leu Gln Ala Asp Thr Asn Ile Ala Met Ile His Ala Ala Asp Lys Arg
        915                 920                 925
Val His Ser Ile Arg Glu Ala Tyr Leu Pro Glu Leu Ser Val Ile Pro
        930                 935                 940
Gly Val Asn Ala Ala Ile Phe Glu Glu Leu Glu Gly Arg Ile Phe Thr
945                 950                 955                 960
Ala Phe Ser Leu Tyr Asp Ala Arg Asn Val Ile Lys Asn Gly Asp Phe
                965                 970                 975
Asn Asn Gly Leu Ser Cys Trp Asn Val Lys Gly His Val Asp Val Glu
            980                 985                 990
Glu Gln Asn Asn His Arg Ser Val Leu Val Val Pro Glu Trp Glu Ala
```

|  |  | 995 |  |  |  | 1000 |  |  |  | 1005 |  |  |
|--|--|--|--|--|--|--|--|--|--|--|--|--|
| Glu | Val | Ser | Gln | Glu | Val | Arg | Val | Cys | Pro | Gly | Arg | Gly | Tyr | Ile | Leu |
|  |  | 1010 |  |  |  | 1015 |  |  |  | 1020 |  |  |

Arg Val Thr Ala Tyr Lys Glu Gly Tyr Gly Glu Gly Cys Val Thr Ile
1025                    1030                1035                        1040

His Glu Ile Glu Asp Asn Thr Asp Glu Leu Lys Phe Ser Asn Cys Val
                1045                    1050                1055

Glu Glu Glu Val Tyr Pro Asn Asn Thr Val Thr Cys Asn Asn Tyr Thr
            1060                    1065                1070

Ala Thr Gln Glu Glu His Glu Gly Thr Tyr Thr Ser Arg Asn Arg Gly
            1075                    1080                1085

Tyr Asp Glu Ala Tyr Glu Ser Asn Ser Ser Val His Ala Ser Val Tyr
        1090                    1095                1100

Glu Glu Lys Ser Tyr Thr Asp Arg Arg Arg Glu Asn Pro Cys Glu Ser
1105                    1110                    1115                        1120

Asn Arg Gly Tyr Gly Asp Tyr Thr Pro Leu Pro Ala Gly Tyr Val Thr
                1125                    1130                    1135

Lys Glu Leu Glu Tyr Phe Pro Glu Thr Asp Lys Val Trp Ile Glu Ile
            1140                    1145                    1150

Gly Glu Thr Glu Gly Thr Phe Ile Val Asp Ser Val Glu Leu Leu Leu
            1155                    1160                    1165

Met Glu Glu
    1170

(2) INFORMATION FOR SEQ ID NO:3:

(i) SEQUENCE CHARACTERISTICS:
        (A) LENGTH: 3513 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
ATGGAGATAG TGAATAATCA GAATCAATGC GTGCCTTATA ATTGTTTAAA TAATCCTGAA      60
AATGAGATAT TAGATATTGA AAGGTCAAAT AGTACTGTAG CAACAAACAT CGCCTTGGAG     120
ATTAGTCGTC TGCTCGCTTC CGCAACTCCA ATAGGGGGGA TTTTATTAGG ATTGTTTGAT     180
GCAATATGGG GGTCTATAGG CCCCTTCACAA TGGGATTTAT TTTAGAGCA AATTGAGCTA     240
TTGATTGACC AAAAAATAGA GGAATTCGCT AGAAACCAGG CAATTTCTAG ATTAGAAGGG     300
ATAAGCAGTC TGTACGGAAT TTATACAGAA GCTTTTAGAG AGTGGGAAGC AGATCCTACT     360
AATCCAGCAT TAAAAGAAGA GATGCGTACT CAATTTAATG ACATGAACAG TATTCTTGTA     420
ACAGCTATTC CTCTTTTTTC AGTTCAAAAT TATCAAGTCC CATTTTTATC AGTATATGTT     480
CAAGCTGCAA ATTTACATTT ATCGGTTTTG AGAGATGTTT CAGTGTTTGG GCAGGCTTGG     540
GGATTTGATA TAGCAACAAT AAATAGTCGT TATAATGATC TGACTAGACT TATTCCTATA     600
TATACAGATT ATGCTGTACG CTGGTACAAT ACGGGATTAG ATCGCTTACC ACGAACTGGT     660
GGGCTGCGAA ACTGGGCAAG ATTTAATCAG TTTAGAAGAG AGTTAACAAT ATCAGTATTA     720
GATATTATTT CTTTTTTCAG AAATTACGAT TCTAGATTAT ATCCAATTCC AACAAGCTCC     780
CAATTAACGC GGGAAGTATA TACAGATCCG GTAATTAATA TAACTGACTA TAGAGTTGGC     840
CCCAGCTTCG AGAATATTGA GAACTCAGCC ATTAGAAGCC CCCACCTTAT GGACTTCTTA     900
AATAATTTGA CCATTGATAC GGATTTGATT AGAGGTGTTC ACTATTGGGC AGGGCATCGT     960
```

| | | | | | |
|---|---|---|---|---|---|
| GTAACTTCTC | ATTTTACAGG | TAGTTCTCAA | GTGATAACAA | CCCCTCAATA | TGGGATAACC | 1020
| GCAAATGCGG | AACCAAGACG | AACTATTGCT | CCTAGTACTT | TTCCAGGTCT | TAACCTATTT | 1080
| TATAGAACAT | TATCAAATCC | TTTCTTCCGA | AGATCAGAAA | ATATTACTCC | TACCTTAGGG | 1140
| ATAAATGTAG | TACAGGGAGT | AGGGTTCATT | CAACCAAATA | ATGCTGAAGT | TCTATATAGA | 1200
| AGTAGGGGGA | CAGTAGATTC | TCTTAATGAG | TTACCAATTG | ATGGTGAGAA | TTCATTAGTT | 1260
| GGATATAGTC | ATCGATTAAG | TCATGTTACA | CTAACCAGGT | CGTTATATAA | TACTAATATA | 1320
| ACTAGCCTGC | CAACATTTGT | TTGGACACAT | CACAGTGCTA | CTAATACAAA | TACAATTAAT | 1380
| CCAGATATTA | TTACACAAAT | ACCTTTAGTG | AAAGGATTTA | GACTTGGTGG | TGGCACCTCT | 1440
| GTCATTAAAG | GACCAGGATT | TACAGGAGGG | GATATCCTTC | GAAGAAATAC | CATTGGTGAG | 1500
| TTTGTGTCTT | TACAAGTCAA | TATTAACTCA | CCAATTACCC | AAAGATACCG | TTTAAGATTT | 1560
| CGTTATGCTT | CCAGTAGGGA | TGCACGAATT | ACTGTAGCGA | TAGGAGGACA | AATTAGAGTA | 1620
| GATATGACCC | TTGAAAAAAC | CATGGAAATT | GGGGAGAGCT | TAACATCTAG | AACATTTAGC | 1680
| TATACCAATT | TTAGTAATCC | TTTTTCATTT | AGGGCTAATC | CAGATATAAT | TAGAATAGCT | 1740
| GAAGAACTTC | CTATTCGTGG | TGGTGAGCTT | TATATAGATA | AAATTGAACT | TATTCTAGCA | 1800
| GATGCAACAT | TGAAGAAGA | ATATGATTTG | GAAAGAGCAC | AGAAGGCGGT | GAATGCCCTG | 1860
| TTTACTTCTA | CAAATCAACT | AGGGCTAAAA | ACAGATGTGA | CGGATTATCA | TATTGATCAA | 1920
| GTTCCAATT | TAGTTGAGTG | TTTATCGGAT | GAATTTTGTC | TGGATGAAAA | GAGAGAATTA | 1980
| TCCGAGAAAG | TCAAACATGC | GAAGCGACTC | AGTGATGAAC | GGAATTTACT | TCAAGATCCA | 2040
| AACTTCAGAG | GGATCAATAG | GCAACCAGAC | CGTGGCTGGA | GAGGAAGCAC | GGATATTACT | 2100
| ATCCAAGGTG | GAGATGACGT | ATTCAAAGAG | AATTACGTCA | CATTACCGGG | TACCTTTGAT | 2160
| GAGTGCTATC | CAACGTATTT | ATATCAAAAA | ATAGATGAGT | CGAAGTTAAA | AGCTTATACC | 2220
| CGCTATGAAT | TAAGAGGGTA | TATCGAGGAT | AGTCAAGACT | TAGAAATCTA | TTTAATTCGC | 2280
| TACAATGCAA | AACACGAGAC | AGTAAACGTG | CCAGGTACGG | GTTCCTTATG | GCCGCTTTCA | 2340
| GCCCAAAGTC | CAATCGGAAA | GTGTGGAGAA | CCGAATCGAT | GCGCGCCACA | CCTTGAATGG | 2400
| AATCCTAATC | TAGATTGCTC | CTGCAGAGAC | GGGGAAAAAT | GTGCCCATCA | TTCCCATCAT | 2460
| TTCTCCTTGG | ACATTGATGT | TGGATGTACA | GACTTAAATG | AGGACTTAGG | TGTATGGGTG | 2520
| ATATTCAAGA | TTAAGACACA | AGATGGCTAT | GCAAGACTAG | GAAATCTAGA | GTTTCTCGAA | 2580
| GAGAAACCAC | TATTAGGGGA | AGCACTAGCT | CGTGTGAAAA | GAGCGGAGAA | AAAATGGAGA | 2640
| GACAAATGCG | AAAAATTGGA | ATGGGAAACA | AATATTGTTT | ATAAAGAGGC | AAAAGAATCT | 2700
| GTAGATGCTT | TATTTGTAAA | CTCTCAATAT | GATAGATTAC | AAGCGGATAC | GAATATCGCG | 2760
| ATGATTCATG | CGGCAGATAA | ACGCGTTCAT | AGCATTCGAG | AAGCGTATCT | GCCAGAGCTG | 2820
| TCTGTGATTC | CGGGTGTCAA | TGCGGCTATT | TTTGAAGAAT | TAGAAGGGCG | TATTTTCACT | 2880
| GCATTCTCCC | TATATGATGC | GAGAAATGTC | ATTAAAAATG | GCGATTTCAA | TAATGGCTTA | 2940
| TCATGCTGGA | ACGTGAAAGG | GCATGTAGAT | GTAGAAGAAC | AGAACAACCA | TCGTTCGGTC | 3000
| CTTGTTGTTC | CAGAATGGGA | AGCAGAAGTG | TCACAAGAAG | TTCGTGTTTG | TCCGGGTCGT | 3060
| GGCTATATCC | TTCGTGTTAC | AGCGTACAAA | GAGGGATATG | GAGAGGGCTG | TGTAACGATT | 3120
| CATGAGATCG | AAGACAATAC | AGACGAACTG | AAATTCAGCA | ACTGTGTAGA | AGAGGAAGTA | 3180
| TATCCAAACA | ACACGGTAAC | GTGTAATAAT | TATACTGCGA | CTCAAGAAGA | ACATGAGGGT | 3240
| ACGTACACTT | CCCGTAATCG | AGGATATGAC | GAAGCCTATG | AAAGCAATTC | TTCTGTACAT | 3300
| GCGTCAGTCT | ATGAAGAAAA | ATCGTATACA | GATAGACGAA | GAGAGAATCC | TTGTGAATCT | 3360

```
AACAGAGGAT ATGGGGATTA CACACCACTA CCAGCTGGCT ATGTGACAAA AGAATTAGAG    3420

TACTTCCCAG AAACCGATAA GGTATGGATT GAGATCGGAG AAACGGAAGG AACATTCATC    3480

GTGGACAGCG TGGAATTACT TCTTATGGAG GAA                                 3513
```

( 2 ) INFORMATION FOR SEQ ID NO:4:

( i ) SEQUENCE CHARACTERISTICS:
    ( A ) LENGTH: 1171 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:4:

| | | | | | | | | | | | | | | |
|---|---|---|---|---|---|---|---|---|---|---|---|---|---|---|
| Met | Glu | Ile | Val | Asn | Asn | Gln | Asn | Gln | Cys | Val | Pro | Tyr | Asn | Cys | Leu |
| 1 | | | | 5 | | | | | 10 | | | | | 15 | |
| Asn | Asn | Pro | Glu | Asn | Glu | Ile | Leu | Asp | Ile | Glu | Arg | Ser | Asn | Ser | Thr |
| | | | 20 | | | | | 25 | | | | | 30 | | |
| Val | Ala | Thr | Asn | Ile | Ala | Leu | Glu | Ile | Ser | Arg | Leu | Leu | Ala | Ser | Ala |
| | | 35 | | | | | 40 | | | | | 45 | | | |
| Thr | Pro | Ile | Gly | Gly | Ile | Leu | Leu | Gly | Leu | Phe | Asp | Ala | Ile | Trp | Gly |
| | 50 | | | | | 55 | | | | | 60 | | | | |
| Ser | Ile | Gly | Pro | Ser | Gln | Trp | Asp | Leu | Phe | Leu | Glu | Gln | Ile | Glu | Leu |
| 65 | | | | | 70 | | | | | 75 | | | | | 80 |
| Leu | Ile | Asp | Gln | Lys | Ile | Glu | Glu | Phe | Ala | Arg | Asn | Gln | Ala | Ile | Ser |
| | | | | 85 | | | | | 90 | | | | | 95 | |
| Arg | Leu | Glu | Gly | Ile | Ser | Ser | Leu | Tyr | Gly | Ile | Tyr | Thr | Glu | Ala | Phe |
| | | | 100 | | | | | 105 | | | | | 110 | | |
| Arg | Glu | Trp | Glu | Ala | Asp | Pro | Thr | Asn | Pro | Ala | Leu | Lys | Glu | Glu | Met |
| | | 115 | | | | | 120 | | | | | 125 | | | |
| Arg | Thr | Gln | Phe | Asn | Asp | Met | Asn | Ser | Ile | Leu | Val | Thr | Ala | Ile | Pro |
| | 130 | | | | | 135 | | | | | 140 | | | | |
| Leu | Phe | Ser | Val | Gln | Asn | Tyr | Gln | Val | Pro | Phe | Leu | Ser | Val | Tyr | Val |
| 145 | | | | | 150 | | | | | 155 | | | | | 160 |
| Gln | Ala | Ala | Asn | Leu | His | Leu | Ser | Val | Leu | Arg | Asp | Val | Ser | Val | Phe |
| | | | | 165 | | | | | 170 | | | | | 175 | |
| Gly | Gln | Ala | Trp | Gly | Phe | Asp | Ile | Ala | Thr | Ile | Asn | Ser | Arg | Tyr | Asn |
| | | | 180 | | | | | 185 | | | | | 190 | | |
| Asp | Leu | Thr | Arg | Leu | Ile | Pro | Ile | Tyr | Thr | Asp | Tyr | Ala | Val | Arg | Trp |
| | | 195 | | | | | 200 | | | | | 205 | | | |
| Tyr | Asn | Thr | Gly | Leu | Asp | Arg | Leu | Pro | Arg | Thr | Gly | Gly | Leu | Arg | Asn |
| | 210 | | | | | 215 | | | | | 220 | | | | |
| Trp | Ala | Arg | Phe | Asn | Gln | Phe | Arg | Arg | Glu | Leu | Thr | Ile | Ser | Val | Leu |
| 225 | | | | | 230 | | | | | 235 | | | | | 240 |
| Asp | Ile | Ile | Ser | Phe | Phe | Arg | Asn | Tyr | Asp | Ser | Arg | Leu | Tyr | Pro | Ile |
| | | | | 245 | | | | | 250 | | | | | 255 | |
| Pro | Thr | Ser | Ser | Gln | Leu | Thr | Arg | Glu | Val | Tyr | Thr | Asp | Pro | Val | Ile |
| | | | 260 | | | | | 265 | | | | | 270 | | |
| Asn | Ile | Thr | Asp | Tyr | Arg | Val | Gly | Pro | Ser | Phe | Glu | Asn | Ile | Glu | Asn |
| | | 275 | | | | | 280 | | | | | 285 | | | |
| Ser | Ala | Ile | Arg | Ser | Pro | His | Leu | Met | Asp | Phe | Leu | Asn | Asn | Leu | Thr |
| | 290 | | | | | 295 | | | | | 300 | | | | |
| Ile | Asp | Thr | Asp | Leu | Ile | Arg | Gly | Val | His | Tyr | Trp | Ala | Gly | His | Arg |
| 305 | | | | | 310 | | | | | 315 | | | | | 320 |
| Val | Thr | Ser | His | Phe | Thr | Gly | Ser | Ser | Gln | Val | Ile | Thr | Thr | Pro | Gln |

|     |     |     |     |     | 325 |     |     |     |     | 330 |     |     |     |     | 335 |
| --- | --- | --- | --- | --- | --- | --- | --- | --- | --- | --- | --- | --- | --- | --- | --- |
| Tyr | Gly | Ile | Thr | Ala | Asn | Ala | Glu | Pro | Arg | Arg | Thr | Ile | Ala | Pro | Ser |
|     |     |     | 340 |     |     |     |     | 345 |     |     |     | 350 |     |     |     |
| Thr | Phe | Pro | Gly | Leu | Asn | Leu | Phe | Tyr | Arg | Thr | Leu | Ser | Asn | Pro | Phe |
|     |     | 355 |     |     |     |     | 360 |     |     |     |     | 365 |     |     |     |
| Phe | Arg | Arg | Ser | Glu | Asn | Ile | Thr | Pro | Thr | Leu | Gly | Ile | Asn | Val | Val |
|     | 370 |     |     |     |     | 375 |     |     |     |     | 380 |     |     |     |     |
| Gln | Gly | Val | Gly | Phe | Ile | Gln | Pro | Asn | Asn | Ala | Glu | Val | Leu | Tyr | Arg |
| 385 |     |     |     |     | 390 |     |     |     |     | 395 |     |     |     |     | 400 |
| Ser | Arg | Gly | Thr | Val | Asp | Ser | Leu | Asn | Glu | Leu | Pro | Ile | Asp | Gly | Glu |
|     |     |     |     | 405 |     |     |     |     | 410 |     |     |     | 415 |     |     |
| Asn | Ser | Leu | Val | Gly | Tyr | Ser | His | Arg | Leu | Ser | His | Val | Thr | Leu | Thr |
|     |     |     | 420 |     |     |     | 425 |     |     |     |     | 430 |     |     |     |
| Arg | Ser | Leu | Tyr | Asn | Thr | Asn | Ile | Thr | Ser | Leu | Pro | Thr | Phe | Val | Trp |
|     |     | 435 |     |     |     |     | 440 |     |     |     |     | 445 |     |     |     |
| Thr | His | His | Ser | Ala | Thr | Asn | Thr | Asn | Thr | Ile | Asn | Pro | Asp | Ile | Ile |
|     | 450 |     |     |     |     | 455 |     |     |     |     | 460 |     |     |     |     |
| Thr | Gln | Ile | Pro | Leu | Val | Lys | Gly | Phe | Arg | Leu | Gly | Gly | Gly | Thr | Ser |
| 465 |     |     |     |     | 470 |     |     |     |     | 475 |     |     |     |     | 480 |
| Val | Ile | Lys | Gly | Pro | Gly | Phe | Thr | Gly | Gly | Asp | Ile | Leu | Arg | Arg | Asn |
|     |     |     |     | 485 |     |     |     |     | 490 |     |     |     |     | 495 |     |
| Thr | Ile | Gly | Glu | Phe | Val | Ser | Leu | Gln | Val | Asn | Ile | Asn | Ser | Pro | Ile |
|     |     |     |     | 500 |     |     |     | 505 |     |     |     |     | 510 |     |     |
| Thr | Gln | Arg | Tyr | Arg | Leu | Arg | Phe | Arg | Tyr | Ala | Ser | Ser | Arg | Asp | Ala |
|     |     |     | 515 |     |     |     |     | 520 |     |     |     | 525 |     |     |     |
| Arg | Ile | Thr | Val | Ala | Ile | Gly | Gly | Gln | Ile | Arg | Val | Asp | Met | Thr | Leu |
|     | 530 |     |     |     |     | 535 |     |     |     |     | 540 |     |     |     |     |
| Glu | Lys | Thr | Met | Glu | Ile | Gly | Glu | Ser | Leu | Thr | Ser | Arg | Thr | Phe | Ser |
| 545 |     |     |     |     | 550 |     |     |     |     | 555 |     |     |     |     | 560 |
| Tyr | Thr | Asn | Phe | Ser | Asn | Pro | Phe | Ser | Phe | Arg | Ala | Asn | Pro | Asp | Ile |
|     |     |     |     | 565 |     |     |     |     | 570 |     |     |     | 575 |     |     |
| Ile | Arg | Ile | Ala | Glu | Glu | Leu | Pro | Ile | Arg | Gly | Gly | Glu | Leu | Tyr | Ile |
|     |     |     | 580 |     |     |     |     | 585 |     |     |     |     | 590 |     |     |
| Asp | Lys | Ile | Glu | Leu | Ile | Leu | Ala | Asp | Ala | Thr | Phe | Glu | Glu | Glu | Tyr |
|     |     | 595 |     |     |     |     | 600 |     |     |     |     | 605 |     |     |     |
| Asp | Leu | Glu | Arg | Ala | Gln | Lys | Ala | Val | Asn | Ala | Leu | Phe | Thr | Ser | Thr |
|     | 610 |     |     |     |     | 615 |     |     |     |     | 620 |     |     |     |     |
| Asn | Gln | Leu | Gly | Leu | Lys | Thr | Asp | Val | Thr | Asp | Tyr | His | Ile | Asp | Gln |
| 625 |     |     |     |     | 630 |     |     |     |     | 635 |     |     |     |     | 640 |
| Val | Ser | Asn | Leu | Val | Glu | Cys | Leu | Ser | Asp | Glu | Phe | Cys | Leu | Asp | Glu |
|     |     |     |     | 645 |     |     |     |     | 650 |     |     |     | 655 |     |     |
| Lys | Arg | Glu | Leu | Ser | Glu | Lys | Val | Lys | His | Ala | Lys | Arg | Leu | Ser | Asp |
|     |     |     | 660 |     |     |     |     | 665 |     |     |     | 670 |     |     |     |
| Glu | Arg | Asn | Leu | Leu | Gln | Asp | Pro | Asn | Phe | Arg | Gly | Ile | Asn | Arg | Gln |
|     |     | 675 |     |     |     |     | 680 |     |     |     |     | 685 |     |     |     |
| Pro | Asp | Arg | Gly | Trp | Arg | Gly | Ser | Thr | Asp | Ile | Thr | Ile | Gln | Gly | Gly |
|     | 690 |     |     |     |     | 695 |     |     |     |     | 700 |     |     |     |     |
| Asp | Asp | Val | Phe | Lys | Glu | Asn | Tyr | Val | Thr | Leu | Pro | Gly | Thr | Phe | Asp |
| 705 |     |     |     |     | 710 |     |     |     |     | 715 |     |     |     |     | 720 |
| Glu | Cys | Tyr | Pro | Thr | Tyr | Leu | Tyr | Gln | Lys | Ile | Asp | Glu | Ser | Lys | Leu |
|     |     |     |     | 725 |     |     |     |     | 730 |     |     |     | 735 |     |     |
| Lys | Ala | Tyr | Thr | Arg | Tyr | Glu | Leu | Arg | Gly | Tyr | Ile | Glu | Asp | Ser | Gln |
|     |     |     | 740 |     |     |     |     | 745 |     |     |     | 750 |     |     |     |

```
Asp Leu Glu Ile Tyr Leu Ile Arg Tyr Asn Ala Lys His Glu Thr Val
        755             760             765
Asn Val Pro Gly Thr Gly Ser Leu Trp Pro Leu Ser Ala Gln Ser Pro
        770             775             780
Ile Gly Lys Cys Gly Glu Pro Asn Arg Cys Ala Pro His Leu Glu Trp
785             790             795             800
Asn Pro Asn Leu Asp Cys Ser Cys Arg Asp Gly Glu Lys Cys Ala His
                805             810             815
His Ser His His Phe Ser Leu Asp Ile Asp Val Gly Cys Thr Asp Leu
            820             825             830
Asn Glu Asp Leu Gly Val Trp Val Ile Phe Lys Ile Lys Thr Gln Asp
        835             840             845
Gly Tyr Ala Arg Leu Gly Asn Leu Glu Phe Leu Glu Glu Lys Pro Leu
        850             855             860
Leu Gly Glu Ala Leu Ala Arg Val Lys Arg Ala Glu Lys Lys Trp Arg
865             870             875             880
Asp Lys Cys Glu Lys Leu Glu Trp Glu Thr Asn Ile Val Tyr Lys Glu
                885             890             895
Ala Lys Glu Ser Val Asp Ala Leu Phe Val Asn Ser Gln Tyr Asp Arg
            900             905             910
Leu Gln Ala Asp Thr Asn Ile Ala Met Ile His Ala Ala Asp Lys Arg
        915             920             925
Val His Ser Ile Arg Glu Ala Tyr Leu Pro Glu Leu Ser Val Ile Pro
    930             935             940
Gly Val Asn Ala Ala Ile Phe Glu Glu Leu Glu Gly Arg Ile Phe Thr
945             950             955             960
Ala Phe Ser Leu Tyr Asp Ala Arg Asn Val Ile Lys Asn Gly Asp Phe
                965             970             975
Asn Asn Gly Leu Ser Cys Trp Asn Val Lys Gly His Val Asp Val Glu
            980             985             990
Glu Gln Asn Asn His Arg Ser Val Leu Val Val Pro Glu Trp Glu Ala
        995             1000            1005
Glu Val Ser Gln Glu Val Arg Val Cys Pro Gly Arg Gly Tyr Ile Leu
    1010            1015            1020
Arg Val Thr Ala Tyr Lys Glu Gly Tyr Gly Glu Gly Cys Val Thr Ile
1025            1030            1035            1040
His Glu Ile Glu Asp Asn Thr Asp Glu Leu Lys Phe Ser Asn Cys Val
                1045            1050            1055
Glu Glu Glu Val Tyr Pro Asn Asn Thr Val Thr Cys Asn Asn Tyr Thr
            1060            1065            1070
Ala Thr Gln Glu Glu His Glu Gly Thr Tyr Thr Ser Arg Asn Arg Gly
        1075            1080            1085
Tyr Asp Glu Ala Tyr Glu Ser Asn Ser Ser Val His Ala Ser Val Tyr
    1090            1095            1100
Glu Glu Lys Ser Tyr Thr Asp Arg Arg Arg Glu Asn Pro Cys Glu Ser
1105            1110            1115            1120
Asn Arg Gly Tyr Gly Asp Tyr Thr Pro Leu Pro Ala Gly Tyr Val Thr
                1125            1130            1135
Lys Glu Leu Glu Tyr Phe Pro Glu Thr Asp Lys Val Trp Ile Glu Ile
            1140            1145            1150
Gly Glu Thr Glu Gly Thr Phe Ile Val Asp Ser Val Glu Leu Leu Leu
        1155            1160            1165
Met Glu Glu
    1170
```

( 2 ) INFORMATION FOR SEQ ID NO:5:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: peptide ( x i ) SEQUENCE DESCRIPTION: SEQ ID NO:5:

GCTGAAGAAC TTCCTATTCG TGGTGGTGAG C          31